United States Patent
Mercep et al.

(10) Patent No.: US 7,384,975 B2
(45) Date of Patent: Jun. 10, 2008

(54) SUBSTITUTED FUROCHROMENES, PREPARATION THEREOF AND THEIR ANTIINFLAMMATORY ACTION

(75) Inventors: Mladen Mercep, Zagreb (HR); Milan Mesic, Zagreb (HR); Boska Hrvacic, Zagreb (HR); Ivaylo Jivkov Elenkov, Zagreb (HR); Ivica Malnar, Gerovo (HR); Stribor Markovic, Zagreb (HR); Lidija Simicic, Zagreb (HR); Andreja Cempuh Klonkay, Zagreb (HR); Anita Filipovic, Zagreb (HR)

(73) Assignee: GlaxoSmithKline Istrazivacki Centar Zagreb d.o.o., Zagreb (HR)

( * ) Notice: Subject to any disclaimer, the term of this patent is extended or adjusted under 35 U.S.C. 154(b) by 103 days.

(21) Appl. No.: 11/337,274

(22) Filed: Jan. 20, 2006

(65) Prior Publication Data

US 2006/0148889 A1  Jul. 6, 2006

Related U.S. Application Data

(63) Continuation of application No. PCT/HR2004/000021, filed on Jul. 22, 2004.

(30) Foreign Application Priority Data

Jul. 25, 2003  (HR)  ............... P 20030604 A

(51) Int. Cl.
  *A61K 31/353*   (2006.01)
  *C07D 311/78*   (2006.01)
  *C07D 407/14*   (2006.01)

(52) U.S. Cl. ............ 514/453; 514/454; 549/276; 549/282

(58) Field of Classification Search ............ 514/453, 514/454; 549/276, 282
  See application file for complete search history.

(56) References Cited

U.S. PATENT DOCUMENTS

| | | | |
|---|---|---|---|
| 4,200,577 A | 4/1980 | Buckle et al. | |
| 4,263,299 A | 4/1981 | Buckle et al. | |
| 4,731,375 A | 3/1988 | Nakano et al. | |
| 5,428,038 A | 6/1995 | Chatterjee et al. | |
| 6,100,409 A | 8/2000 | Trkovnik et al. | |

FOREIGN PATENT DOCUMENTS

| | | |
|---|---|---|
| HR | P20030603 A | 10/2005 |
| JP | 50046666 | 4/1975 |
| WO | WO-92/13872 | 8/1992 |
| WO | WO-92/13873 | 8/1992 |
| WO | WO-94/13690 | 6/1994 |
| WO | WO-94/14834 | 7/1994 |
| WO | WO-03/029237 | 4/2003 |
| WO | WO-2005/010006 | 2/2005 |

OTHER PUBLICATIONS

Zhao, H. et al., "Coumarin-Based Inhibitors of HIV Integrase" J Med. Chem. 1997, 40, pp. 242-249.

*Primary Examiner*—Taofiq Solola
(74) *Attorney, Agent, or Firm*—J. Michael Strickland

(57) ABSTRACT

The invention relates to novel compounds of the formula (I)

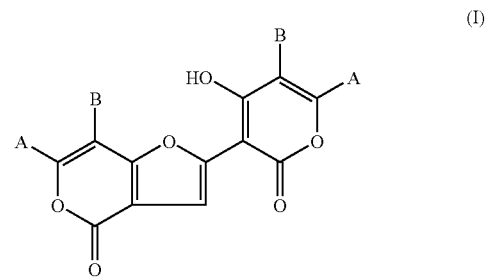

including all their tautomers, to pharmaceutically acceptable salts and solvates thereof, to processes and reactive intermediates for the preparation thereof, and to processes and reactive intermediates for the preparation of the compounds of the formula (II) including all their stereoisomers and tautomers

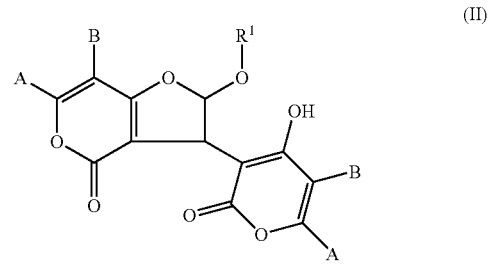

to the use of the compounds of the formula (II) as suitable precursors for the preparation of the compounds of the formula (I) as well as to use of the compounds of the formula (I) and of the compounds of the formula (II) as therapeutically active agents in the prophylaxis and treatment of asthma and other inflammatory diesases and conditions in humans.

14 Claims, No Drawings

SUBSTITUTED FUROCHROMENES, PREPARATION THEREOF AND THEIR ANTIINFLAMMATORY ACTION

This application is a continuation of PCT International Patent Application No. PCT/HR2004/000021, filed Jul. 22, 2004, which claims priority of Croatian Patent Application No. P20030604A, filed Jul. 25, 2003.

FIELD OF THE INVENTION

The invention relates to novel compounds of formula (I)

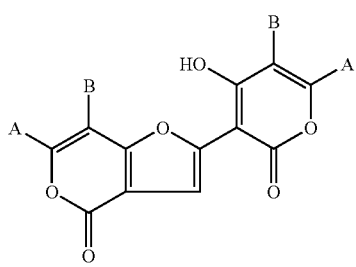

(I)

including tautomers thereof, to their pharmaceutically acceptable salts and solvates, to processes and reactive intermediates for the preparation thereof, further to processes and reactive intermediates for the preparation of compounds of formula (II)

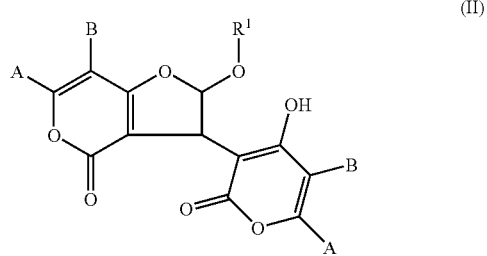

(II)

including all stereoisomers and tautomers thereof, to the use of the compounds of the formula (II) as suitable precursors for the preparation of the compounds of the formula (I), as well as to the use of the compounds of the formula (I) and of the compounds of the formula (II) as therapeutically active agents in the prophylaxis and treatment of asthma and other inflammatory diseases and conditions in humans.

BACKGROUND OF THE INVENTION

Asthma is a chronic inflammatory disease of respiratory airways in humans. Clinically, in hypersensitive persons the inflammation causes periodical coughing attacks, troubled breathing, wheezing, tightness in the chest and chest pain. The inflammation makes respiratory airways more susceptible to irritations by allergens, chemical irritants, tobacco smoke, cold air and strain. Exposed to these irritants respiratory airways become edematous, contracted, filled with mucus and hypersensitive.

The pathogenesis of asthma is complex and includes the interaction of inflammatory cells, mediators as well as of the tissue and cells of respiratory airways. In asthmatic process an early phase and a late phase of a response are distinguished. Allergic diseases as well as allergen-induced asthma are characterised by the synthesis of a specific type of IgE antibodies. Immediately after the inhalation of allergens, complexes of allergens and allergen specific IgE's are bound to highly affinity IgE receptor (Fcε receptor type I) present on basophils, mastocytes and eosinophils. By the binding to the receptor the activation of signal transfer cascade occurs, which results in:

1. de novo synthesis of proinflammatory genes (e.g. interleukin-4 and interleukin-5),
2. egocytosis of the content of cytoplasmatic granules—degranulation.

The granules contain inflammatory mediators such as histamine, serotonin, leukotrienes C4, D4 and E4, and proteins such as major basic protein and mieloperoxidase. These inflammatory mediators co-operate in the processes of vasodilation, bronchoconstriction, triggering and control of the inflammatory process and activation of the cells and damage to the inflamed tissue. These processes form the early asthmatic response. The inhibition of degranulation may prevent the symptoms and stop the inflammation progress, which has been proven by the clinical use of degranulation inhibitors (sodium chromoglycate, nedocromyl sodium and ketotifen).

The late asthmatic response includes a permanent obstruction of air passages, a hyperreactivity of the bronchi and a development of inflammation changes including the accumulation of neutrophils, eosinophils, lymphocytes and monocytes/macrophages in the respiratory system. The accumulation of inflammatory cells results from harmonized interaction of lymphokines (TNF-α, IL-4, IL-5), adhesion molecules on the surface of leukocytes (integrins) and endothelial cells (selectins), and chemokines (eotaxin, RANTES). The role and significance of T-lymphocytes in asthma were confirmed by the existence of an increased number of activated CD4+ T-cells in bronchoalveolar lavage and bronchial biopsies of patients suffering from asthma. Two subpopulations of CD4+ cells differ with regard to the profile of cytokines they secrete. Th 1 cells secrete IL-2, IL-3, GM-CSF, INF-γ. An activation of Th 1 cells is important in the defence of the host against intracellular organisms, viruses and neoplasms. Investigations have demonstrated that, in asthma, Th 2 cell response prevails with an increased expression of IL-5 that is important in the formation of eosinophilic infiltration typical of allergic inflammation.

Morphologic changes occurring in asthma include an infiltration of the bronchi by inflammation cells (mastocytes, T-lymphocytes and eosinophils are the key executive cells), a clogging of respiratory airways by a secrete, interstition oedema and increased microcirculation permeability. On the basis of pathophysiological findings it has been established that eosinophilic infiltration is specific and differentiates asthma from other types of inflammation.

In the control of asthma two types of medicaments exists, symptomatic ones and basic ones. The symptomatic medicaments include short-acting bronchodilators such as β2-agonists, anticholinergics, teophilin, which rapidly relax the contracted respiratory airways and alleviate the acute symptoms. The basic medicaments include antiinflammatory drugs and long-acting bronchodilators. Antiinflammatory drugs alleviate and prevent the inflammation reaction and they include inhalation corticosteroids, systemic corticosteroids, inhalations of sodium chromoglycate and nedochromil.

Steroid antiinflammatory compounds are still considered to be the most effective medicaments in the treatment of inflammatory diseases and conditions such as asthma. The good potency and efficacy of said type of medicaments are, however, accompanied by numerous undesired side effects, such as disturbances of carbohydrate metabolism, of calcium resorption, of the secretion of endogenic corticosteroids and of physiological functions of the hypophysis, of the suprarenal gland core and of the thymus. In the literature (WO 94/13690, WO 94/14834, WO 92/13872 and WO 92/13873) so-called "soft" steroids or hydrolysable corticosteroids with local action are described. Their systemic, undesired effect is reduced due to the instability of "soft" steroids in serum, where the active steroid is rapidly hydrolyzed to an inactive form. However, a steroid without negative side effects in long-term use still has to be found.

Some compounds of coumarin class (U.S. Pat. Nos. 4,200,577; 4,263,299; 4,731,375; 5,428,038) show antiallergic action in the prevention and treatment of various allergic diseases such as allergic asthma, allergic dermatitis, allergic rhinitis or enteritis, allergic conjunctivitis or allergic eczema.

There are also known more complex dimer and tetramer derivatives of hydroxycoumarin asymmetrically bound by a central alkyl or aryl linker, which demonstrate anti-HIV action (Zhao, H. et al. *J. Med. Chem.* 1997, 40, 242-249). Similar anti-HIV action is also shown by several products of condensation of hydroxycoumarins possessing more than one hydroxy group per coumarin unit with aromatic or aliphatic mono- or dialdehydes (U.S. Pat. No. 6,100,409 and WO 03/029237).

SUMMARY OF THE INVENTION

Compounds that are the most similar to the ones of the present invention are described in WO 03/029237 and relate to 3-(4,7-dihydroxy-2-oxo-2H-chromene-3-yl)-7-hydroxy-2,3-dihydro-furo[3,2-c]chromene-4-ones, wherein the C/2 position of the furan ring is substituted with a methoxy or ethoxy group. Said compounds are prepared by condensation of corresponding hydroxycoumarins and glyoxal in an alcohol-water medium at high temperatures, whereat in the course of the reaction a simultaneous binding of the alcohol and the formation of a corresponding alkoxy substituent occur.

Now it has been found that compounds having a methoxy group in C/2 position of the furan ring can be obtained by condensation of corresponding hydroxycoumarins and dimethoxyacetaldehyde. It has been found as well that compounds with C/2 substituents such as hydroxy (described in HR patent application No. P20030603A of the same applicant), methoxy or ethoxy (in broader sense alkoxy) may serve as suitable starting compounds for the preparation of compounds having another coumarin unit substituted in C/2 position of the furan ring. Besides, it has turned out that compounds of this type also have an interesting antiinflammatory action.

According to our knowledge and the established prior art, compounds having another coumarin unit substituted in the furan ring in C/2 position, and wherein the coumarin rings, in addition to or instead of hydroxy groups, also have other substituents such as alkyl and alkyloxy groups and halogen atoms, which are represented by the formula (I), as well as their pharmaceutically acceptable salts and pharmaceutical preparations including them in their composition, have hitherto not been described. Likewise, the compounds of the present invention have not been described as substances with a strong antiinflammatory action or as effective agents in the treatment of asthma and other inflammatory diseases and conditions.

The applied in vitro and in vivo models quite successfully demonstrate pathophysiological occurrences present in asthma and it may be expected that the compounds tested in these models will also be effective in the therapy of human diseases.

The present invention particularly relates to novel compounds of the formula (I)

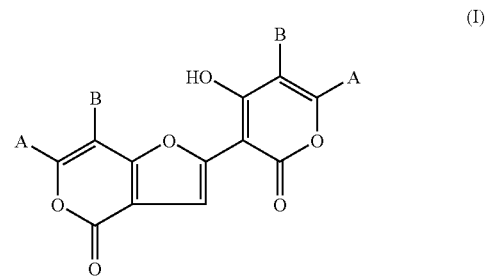

wherein

A and B together with C-atoms to which they are bound represent an aromatic moiety, which may have one, two or more identical or different substituents, which may be halogen, $C_1$-$C_4$-alkyl, $C_2$-$C_4$-alkenyl, $C_2$-$C_4$-alkynyl, halo-$C_1$-$C_4$-alkyl, hydroxy, $C_1$-$C_4$-alkoxy, trifluoromethoxy, $C_1$-$C_4$-alkanoyl, amino, amino-$C_1$-$C_4$-alkyl, N-($C_1$-$C_4$-alkyl) amino, N,N-di($C_1$-$C_4$-alkyl) amino, sulfanyl, $C_1$-$C_4$-alkylsulfanyl, sulfo, $C_1$-$C_4$-alkylsulfo, sulfino, $C_1$-$C_4$-alkylsulfino, carboxy, $C_1$-$C_4$-alkoxycarbonyl, cyano, nitro;

or they may be further condensed with optionally substituted heteroaromatic moieties or heterocycles.

The objects of the present invention are:
a) compounds of the formula (I),
b) processes and reactive intermediates for the preparation of the compounds of the formula (I),
c) processes for the preparation the compounds of formula (II) and use thereof as precursors for the preparation of the compounds of the formula (I),
d) mixtures of the prepared compounds of the formula (I) and of the formula (II) in amounts sufficient for suppressing inflammatory processes and conditions,
e) methods of use of the prepared compounds of the formula (I) and of the formula (II) in the treatment of disorders and conditions induced by inflammatory processes.

DETAILED DESCRIPTION OF THE INVENTION

In the context of the present invention the used general terms mainly have the following meanings:

The term "halogen" relates to a halogen atom which may be: fluorine, chlorine, bromine or iodine.

The term "alkyl" relates to alkyl groups having the meaning of alkanes, wherefrom radicals are derived, which may be straight, branched or cyclic or a combination of straight and cyclic ones or of branched and cyclic ones. The preferred straight or branched alkyls are e.g. methyl, ethyl, propyl, isopropyl, butyl, sec-butyl and tert-butyl. The preferred cyclic alkyls are e.g. cyclopentyl or cyclohexyl. Alkyl may be optionally additionally substituted with one, two, three or more substituents. Such substituents may be a halogen atom (preferably fluorine or chlorine), hydroxy, $C_1$-$C_4$-alkoxy (preferably methoxy or ethoxy), sulfanyl, $C_1$-$C_4$-alkylsulfanyl (preferably methylsulfanyl or ethylsulfanyl), amino, N-($C_1$-$C_4$)alkylamino (preferably N-methylamino or N-ethylamino), N,N-di($C_1$-$C_4$-alkyl)amino (preferably dimethylamino or diethylamino), sulfo, $C_1$-$C_4$-alkylsulfo (preferably methylsulfo ili ethylsulfo), sulfino, $C_1$-$C_4$-alkylsulfino (preferably methylsulfino).

The term "alkenyl" relates to alkenyl groups having the meaning of hydrocarbon radicals, which may be straight, branched or cyclic or are a combination of straight and cyclic ones or of branched and cyclic ones, but have at least one carbon-carbon double bond. The most frequent alkenyls are ethenyl, propenyl, butenyl or cyclohexenyl. Alkenyl may be optionally additionally substituted with one, two or three halogen atoms. Such substituents may be e.g. 2-chloroethenyl, 1,2-dichloroethenyl or 2-bromopropen-1-yl.

The term "alkynyl" relates to alkynyl groups having the meaning of hydrocarbon radicals, which are straight or branched and contain at least one and at most two carbon-carbon triple bonds. The most frequent alkynyls are e.g. ethynyl, propynyl or butynyl.

The term "alkoxy" relates to straight or branched chains of alkoxy group. Examples of such groups are methoxy, propoxy, prop-2-oxy, butoxy, but-2-oxy or methylprop-2-oxy.

The term "aromatic moiety" relates to the radicals of an aromatic ring e.g. benzene, as well as to other condensed aromatic rings. The aromatic moiety contains one ring with at least 6 carbon atoms or two rings with totally 10 carbon atoms and alternating double (resonant) bonds between carbon atoms. The most frequently used aromatic moieties are e.g. benzene or naphthalene rings. Aromatic groups are linked to A and B sites of the rest of the molecule via any two available adjacent carbon atoms. Under the term aromatic moiety there is also to be understood a benzene ring, which may optionally be condensed by cycloalkanes, most frequently cyclohexane.

The term "heteroaromatic moiety" relates to groups having the meaning of aromatic and partially aromatic groups of a monocyclic or bicyclic ring with 4 to 12 atoms, at least one of them being a hetero atom such as O, S or N, wherein two available adjacent carbon atoms are the binding site of the group to the A and B sites of the rest of the molecule. Examples of this type are thiophene, pyrrole, imidazole, pyridine, oxazole, thiazole, pyrazole, tetrazole, pyrimidine, pyrazine, quinoline or triazine rings.

The term "heterocycle" relates to five-member or six-member, fully saturated or partially unsaturated heterocyclic groups containing at least one hetero atom such as O, S or N, wherein two available adjacent carbon atoms are the binding site of the group to the A and B sites of the rest of the molecule. The most frequent examples are morpholinyl, piperidinyl, piperazinyl, pyrrolidinyl, pirazinyl or imidazolyl.

The term "alkanoyl" group relates to straight chains of acyl group such as formyl, acetyl or propanoyl.

The term "aroyl" group relates to aromatic acyl groups such as benzoyl.

The heteroaromatic moiety or heterocycle may be optionally additionally substituted with one, two or more substituents. Substituents may be halogen (fluorine, chlorine, iodine or bromine) $C_1$-$C_4$-alkyl (preferably methyl, ethyl or isopropyl), trifluoromethyl, cyano, nitro, hydroxy, $C_1$-$C_4$ alkoxy (preferably methoxy or ethoxy), $C_1$-$C_4$-alkyloxycarbonyl (preferably methyloxycarbonyl), sulfanyl, $C_1$-$C_4$-alkylsulfanyl (preferably methylsulfanyl or ethylsulfanyl), amino, N-($C_1$-$C_4$) alkylamino (preferably N-methylamino or N-ethylamino), N,N-di($C_1$-$C_4$-alkyl)amino (preferably N,N-dimethylamino or N,N-diethylamino), sulfo, $C_1$-$C_4$ alkylsulfo (preferably methylsulfo or ethylsulfo), sulfino, $C_1$-$C_4$ alkylsulfino (preferably methylsulfino).

A further object of the present invention relates to pharmaceutically acceptable salts of the compounds of the formula (I). The compounds representing an object of the present invention comprise at least one acidic hydroxyl group on a coumarin nucleus and thus can form salts with pharmaceutically acceptable bases. Examples of such salts formed on a hydroxyl substituent are e.g. aluminum salts, corresponding salts of alkali metals such as sodium or potassium, salts of earth alkali metals such as calcium or magnesium, pharmaceutically acceptable salts of transient metals such as zinc and copper, salts with ammonia or salts with lower organic amines such as cyclic amines, mono-, di- or trisubstituted lower alkylamines, further lower hydroxyalkylamines such as lower mono-, di- or trihydroxyalkylamines, lower (hydroxyalkyl)alkylamines or lower polyhydroxyalkylamines and salts with amino acids e.g. methylglutamine, alanine or serine. Cyclic amines are e.g. morpholine, thiomorpholine, piperidine or pyrrolidine. Suitable lower monoalkylamines are e.g. ethylamine and tert-butylamine, suitable dialkylamines are e.g. diethylamine and diisopropylamine and suitable lower trialkylamines are e.g. trimethylamine and triethylamine. Corresponding lower hydroxyalkylamines are e.g. mono-, di- or triethanolamine; lower (hydroxyalkyl) alkylamines are e.g. N,N-dimethylaminoethanol and N,N-diethylaminoethanol. Amino acids are e.g. lysine, arginine, methylglutamine, alanine or serine. These salts may be prepared in situ during the final isolation and purification of the compounds of the present invention or separately in a reaction with suitable inorganic or organic base in a manner know to the one skilled in the art.

The prefix "lower" denotes a chain having up to and including seven, especially up to and including four carbon atoms. Lower alkyls are e.g. n-propyl, isopropyl, n-butyl, isobutyl, sec-butyl, tert-butyl, n-pentyl, neopentyl, n-hexyl or n-heptyl and most frequently ethyl or methyl.

In view of the close connection between free forms and salt forms of the compounds represented by the formula (I), it should be understood that in the present invention the free forms of the compounds represented by the formula (I) and their salts are identical forms and in the corresponding context it is suitable to consider the free forms of the compounds of the present invention and their corresponding salts as synonymous.

The present invention also relates to solvates (most frequently hydrates) that can be formed by the compounds of the formula (I) or their salts.

The compounds represented by the formula (I) and their salts may exist in different physical forms (e.g. in different crystal forms) and the present invention relates to all physical forms (e.g. to all crystal forms) of the compounds represented by the formula (I) and to their mixtures.

The present invention comprises all prodrug forms of the compounds of the formula (I) i.e. compounds, which upon in vivo application in mammals release the active medicinal substance of the formula (I) in the organism. The prodrug forms can be prepared by the modification of any functional group present in a compound of the formula (I) in such a manner that the modified group may be easily disintegrated in vivo while releasing the starting active compound. The hydroxy group is a suitable site for the formation of prodrug forms of such compounds.

Thanks to a large number of various substituents and possible tautomerization, some compounds of the present invention may exist in different isomeric forms, whereby different tautomeric forms, but also different geometric isomers and stereoisomers are to be understood. Isomers, which differ only with regard to the arrangement of the atoms in the space around the asymmetric (chiral) centre are called "stereoisomers". Two stereoisomers that do not correlate as a subject and its mirror image are called "diastereoisomers", whereas the ones that correlate as a subject and its mirror image are called "enantiomers". Each enantiomer can be characterised by determining the absolute configuration of the asymmetric centre by the use of Cahn-Ingold-Prelog priority rule and hence characterised as R- or S-isomer. Another way of identification of stereoisomers is the measurement of the rotation of the plane of the polarised light passing through the molecule, namely as a right-rotating (+)-isomer or a left-rotating (−)-isomer. Chiral compounds may exist as single enantiomers or as a mixture of enantiomers. A mixture containing equal proportions of enantiomers is called a "racemic mixture". The present invention relates to all stereoisomers that can be represented by the formula (I), either the ones isolated as single enantiomers or the ones present in a racemic or some other mixture. The methods of determination of stereochemical configuration and separation of stereoisomers are well known from the literature.

The compounds of the formula (I) may also form two or more structural isomers, which are in equilibrium, but may be formed as a consequence of tautomerism. Due to the dynamic equilibrium such isomers (tautomers) can easily be transformed from one isomeric form to another. Which of the isomeric forms will prevail in the mixture depends on the kind of compound, on whether the compound is in free form or in the form of any of its salts, on the type of the salt, on the solvent, in which the compound is dissolved, as well as on the pH value of the solution. In the present invention under the term compounds of the formula (I) there should also be understood all tautomeric forms, either isolated separately or in a mutual equilibrium mixture of various proportions.

Methods of Preparation

A further object of the present invention relates to a process for the preparation of the compounds of the formula (I) and salts thereof comprising rearranging the compounds of the formula (II)

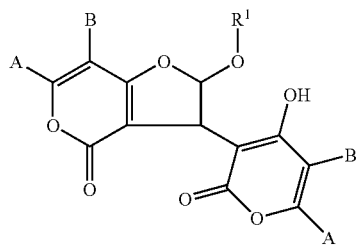

wherein $R^1$ has the meaning of hydrogen atom or alkyl, in an acidic medium in an optimum temperature range and/or, optionally, converting the formed free compounds represented by the formula (I) into corresponding salts, and/or optionally converting the formed salts into free compounds or into other salts.

The compounds of the formula (I) are formed by intramolecular rearrangement of the compounds of the formula (II) in an acidic medium. As acids there are used lower organic acids, preferably acetic acid, which simultaneously serves as a solvent. Reactions are carried out at temperatures from room temperature to 150° C. (in case of acetic acid most appropriately at its boiling temperature). The duration of the reactions is from 1 to 24 hours depending on the reaction temperature (in case of boiling acetic acid 1 hour is sufficient). Most frequently by cooling the reaction mixture a product is precipitated, which may then be easily separated by filtration by suction and purified by washing and drying. Other methods of isolation and purification, which are common in preparative organic chemistry, may be used as well.

As precursors in the synthesis of two compounds of the formula (I) there are used the compounds of the formula (II), wherein $R^1$ is methyl and A and B together with C-atoms, to which they are bound represent an unsubstituted benzene ring or a benzene ring substituted by one hydroxyl group. These compounds are described in WO 03/029237. The remaining derivatives of the formula (II) having an alkoxy substituent in C/2 position of the furan ring and used in the synthesis of the compounds of the formula (I), have hitherto not been described. Compounds of the formula (II) having an alkoxy substituent in C/2 position of the furan ring may be prepared by condensing substituted hydroxycoumarins and glyoxal in an alcohol according to the process described in the above-mentioned patent application. C/2-Alkoxy derivatives of the formula (II) may also be prepared by alkylating the compounds of the formula (II) wherein $R^1$ is a hydrogen atom. These compounds are the object of another patent application by the same applicant (HR patent application No. P20030603A). It has, however, now been found that the compounds of the formula (II) having a methoxy group in C/2 position of the furan ring, may be prepared by condensing substituted hydroxycoumarins and dimethoxyacetaldehyde. This method of the preparation of the compounds of the formula (II) has proven to be more efficient because products of a higher purity are obtained in higher yields.

Thus, a further object of the present invention are processes for the preparation of the compounds of the formula (II)

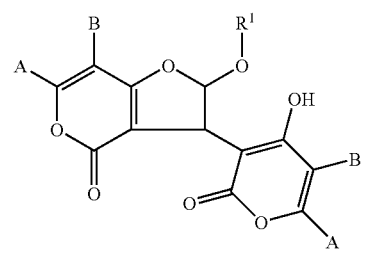

including all their stereoisomers and tautomers, wherein

A and B together with C-atoms to which they are bound represent an aromatic moiety which may have one, two or more identical or different substituents, which may be halogen atom, $C_1$-$C_4$-alkyl, $C_2$-$C_4$-alkenyl, $C_2$-$C_4$-alkynyl, halo-$C_1$-$C_4$-alkyl, hydroxy, $C_1$-$C_4$-alkoxy, trifluoromethoxy, $C_1$-$C_4$-alkanoyl, amino, amino-$C_1$-$C_4$-alkyl, N-($C_1$-$C_4$- alkyl)amino, N,N-di($C_1$-$C_4$-alkyl)amino, sulfanyl, $C_1$-$C_4$-alkylsulfanyl, sulfo, $C_1$-$C_4$-alkylsulfo, sulfino, $C_1$-$C_4$-alkylsulfino, carboxy, $C_1$-$C_4$-alkoxycarbonyl, cyano, nitro; or which may further be condensed by optionally substituted heteroaromatic moieties or heterocycles, and $R^1$ has the meaning of methyl, characterized in that the processes comprise condensing compounds of formula (III) or salts thereof

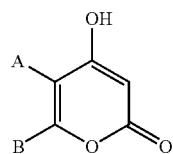

with dimethoxyacetaldehyde of the formula (IV)

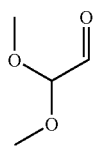

in aqueous-organic medium; and/or converting the formed free compounds represented by the formula (II) into corresponding salts, and/or converting the formed salts into free compounds or other salts.

The used organic solvent may be acetonitrile, acetone, ethanol or methanol and the temperature of the reaction mixture is the boiling temperature of the solvent.

In order to avoid undesired participation in chemical reactions it is often necessary to protect, prior to the reaction, certain reactive groups such as some of the hydroxy groups that can be present in hydroxycoumarins, or one of the two aldehyde groups of glyoxal. For this purpose a great number of protecting groups (Green, T. W.; Wuts, P. G. M., Protective Groups in Organic Synthesis, John Wiley and Sons, 1999) can be used. Their selection, use and removal after performed reaction are usual methods in chemical synthesis.

The salts of compounds of formula (I) can be prepared by commonly known processes such as a reaction of compounds of the formula (I) with a corresponding base in a suitable solvent or solvent mixture e.g. ethers (diethylether) or alcohols (ethanol, propanol or isopropanol), or by mixing equivalent amounts of reactants and a subsequent lyophilization and purification of the mixture.

The present invention also relates to reactive intermediates, which are prepared during the preparation of compounds of the formula (I) and of their pharmaceutically acceptable salts. Such intermediates can be isolated and defined or used without isolation in a further phase of chemical synthesis.

A further object of the present invention relates to the use of compounds of the formula (I) and their pharmaceutically acceptable salts in therapeutically effective amounts in the prophylaxis and treatment of diseases and/or conditions resulting from disorders of immunological system, especially inflammatory diseases and conditions (especially asthma) in humans.

A further object of the present invention relates to the use of compounds of the formula (I) and their pharmaceutically acceptable salts as antiinflammatory, antianaphylactic and immunomodulating agents, which—depending on the site of disease—can be differently administered, e.g. per os, parenterally, percutaneously, buccally, rectally or by inhalation in case of local application.

Pharmaceutical Compositions

A further object of the present invention relates to the preparation of pharmaceutical forms of the present compounds formulated in such a manner as to achieve an optimal bioavailability of the active compounds of the formula (I). For percutaneous application the compounds of the formula (I) can be formulated in the form of an ointment, cream, gel or lotion. Ointments, creams and gels can be formulated with a water base or an oil base under the addition of a suitable emulsifier or gelling agent when gel is formulated. The formulation is especially important for the use by inhalation, wherein compounds of the formula (I) can be in the form of aerosol under pressure. For all forms of aerosol formulations there is suggested a micronization of the compounds of the formula (I) being previously homogenized in lactose, glucose, higher fatty acids, sodium salt of dioctylsulfosuccinic acid or most preferably in carboxymethylcellulose, so that the majority of the particles have the size of 5 µm. For the inhalation formulation the aerosol can be mixed with a propellant intended for the spraying of the active substance.

For the inhalation application the compounds of the formula (I) can be used in the form of a dry powder with micronized particles.

Suitable preparations of the compounds of the formula (I) and of the formula (II) of the present invention can be used in the prophylaxis and treatment of several inflammatory diseases and pathological allergic conditions. Examples of such conditions and diseases are, without limitation, asthma, chronic obstructive pulmonary disease, inflammatory nasal diseases such as allergic rhinitis, nasal polyps, dermatological inflammations such as eczemas, psoriasis, allergic dermatitis, neurodermatitis, pruritis, conjunctivitis rheumatoid arthritis, bowel diseases such as Crohn's disease, colitis and ulcerative colitis, further insulin-dependent diabetes, autoimmune thyroiditis, lupus erythematosus, multiple sclerosis, Raynaud's disease, rheumatoid spondylitis, septic arthritis, polyarthritis, retinitis, inflammatory brain diseases such as meningitis and encephalitis, conditions induced by acute trauma such as brain, miocard and lung lesions, inflammations accompanying infections such as sepsis, glomerulonephritis.

The compounds of the formula (I) and of the formula (II) can be used induvidually or in combination with any other commercial product suitable for treating said diseases and/or conditions.

The compounds of the formula (I) and of the formula (II) possess useful pharmacological properties supported by in vitro and in vivo investigations disclosed in the continuation of the present invention.

Biological Assays

Analysis Method of Inhibition of RBL-2H3 Cell Degranulation

RBL-2H3 cell line of rat basophilic leukaemia (ATCC) was used for the investigation of inhibition of degranulation induced by the activation of Fcε receptor type I or calcium ionophors. RBLL-2H3 cell line was cultivated in DMEM medium (Invitrogen Cat. No. 31966-021) with 10% of fetal calf serum (Invitrogen Corporation) at 37° C., 5% $CO_2$, 90% relative humidity. Cells were seeded in the same medium into 24-well plates, 50000 per well, and left to reach 80-90% of confluence.

Dilutions of compounds were prepared in DMEM medium without phenol red (Invitrogen Corporation) in concentrations from 200 µM to 1 µM. The medium was removed from the cells and the dilutions of compounds were added thereto with the exception of the positive and the negative control where pure DMEM medium was added. Subsequently, to all wells there were added:
1. for the IgE-induced degranulation by Fcε receptor type I, a solution of SPE-1 (dinitrophenyl specific IgE) antibodies (Sigma) and dinitrophenylalbumin (Sigma), both in a final concentration of 0.5 μg/mL,
2. for $Ca^{2+}$-induced degranulation by means of a calcium ionophor, the solution A23187 (Calbiochem) in a final concentration of 250 ng/ml, with the exception of the negative control wells, wherein pure DMEM medium was added. The cells were incubated for one hour at 37° C., 5% $CO_2$, 90% relative humidity. Each dilution as well as the positive and the negative controls were performed in triplicate.

The supernatant (50 μL) was transferred in duplicate to a 96-well plate. Thereto 100 μL of 50 mM sodium citrate buffer with 1 mg/mL para-nitrophenyl-N-acetyl-β-D-glucosaminide (Calbiochem) were added and it was incubated for 1 hour at 37° C. The reaction was stopped with 100 μL of a saturated sodium carbonate solution. The absorbance was measured at 405 nm. The percentage of inhibition was expressed by the formula:

% inh=(1−($OD_{405}$sample−$OD_{405}$negative control)/($OD_{405}$positive control−$OD_{405}$negative control))*100.

The majority of the compounds inhibited the degranulation of RBL-2H3 cells, but most active were the compounds 6, 8, 13, 20, P5, P7, P12, P14, P19, P21, P23, P27 and P28 demonstrating an action in doses from 100-3 μM. Ketotifen as a standard inhibits degranulation in concentrations from 200-50 μM Model of Lung Eosinophilia in Mice Male Balb/C mice (Charles River) of 20-25 g of body weight were randomly divided into groups. They were sensitized by i.p. application of ovalbumin (Sigma) on days zero and fourteen. On day twenty the mice were subjected to a provocative test by i.n. application of ovalbumin (positive control and test groups) or PBS (negative control). After 48 hours the animals were anesthetized and the lungs were rinsed with 1 mL of PBS. The cells were centrifuged on Cytospin 3 cytocentrifuge (Shandon). Then the cells were stained with Diff-Quick (Dade) and the percentage of eosinophils was determined by differential counting of at least 100 cells.

Beclomethazone was used as a standard substance in addition to positive and negative controls. The compound was applied daily i.n. in a dose of 2 mg/kg for 2 days prior to the provocative test and until the end of the investigation.

The compound 13 reduced the number of eosinophils in the lavage and histological preparations of lungs for 50% in relation to the positive control group.

EXAMPLES

The present invention is illustrated by the following Examples, which are given only as illustrative examples and do not limit the scope of the invention in any way. The preparation processes were mostly carried at atmospheric pressure and at room temperature. In each example the final product was characterised by means of one or several of the following methods: high-performance liquid chromatography (HPLC) and/or high-performance liquid chromatography connected to a mass spectrometer (HPLC-MS) and/or high resolution mass spectrometry (HR-MS) and spectroscopy of nuclear magnetic resonance (NMR). Temperatures were expressed in Celsius degrees and the reaction time in hours: DMSO=dimethylsulfoxide.

Compound 1: 2-(4-Hydroxy-2-oxo-2H-chromene-3-yl)-4H-furo[3,2-c]chromene-4-one

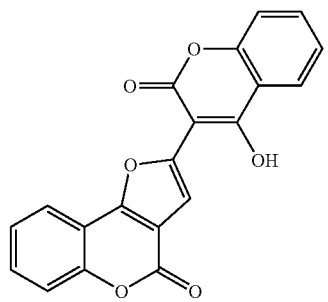

Example 1

2-Ethoxy-3-(4-hydroxy-2-oxo-2H-chromene-3-yl)-2,3-dihydro-4H-furo[3,2-c]-chromene-4-one (840 mg; 2.14 mmole) was suspended in acetic acid (10 mL). The reaction mixture was refluxed for 1 hour, whereat the starting material was dissolved, and then a yellow precipitate was formed. The reaction mixture was cooled to room temperature and the precipitate formed by cooling was filtered off, washed with acetic acid and diethylether, and dried. Obtained were 340 mg (45%) of substance 1:

$^1$H-NMR (300 MHz, DMSO-$d_6$) δ/ppm: 7.28 (s, 1H); 7.39-7.49 (m, 3H); 7.52-7.79 (m, 3H); 7.96 (dd, J=7.8 Hz, J=1.4 Hz, 1H); 8.09 (dd, J=8.2 Hz, J=1.7 Hz, 1H);

$^{13}$C-NMR (75 MHz, DMSO-$d_6$) δ/ppm: 108.2; 110.0; 112.0; 115.9; 116.2; 116.6; 120.6; 123.7; 123.9; 124.4; 130.4; 132.8; 149.7; 151.7; 151.9; 152.3; 155.6; 159.6; 163.6 and 156.7;

ES$^-$ m/z (acetonitrile:water) [M-H]$^-$ 345.0.

Compound 2: 2-(4-Hydroxy-6-methyl-2-oxo-2H-chromene-3-yl)-8-methyl-4H-furo[3,2-c]chromene-4-one

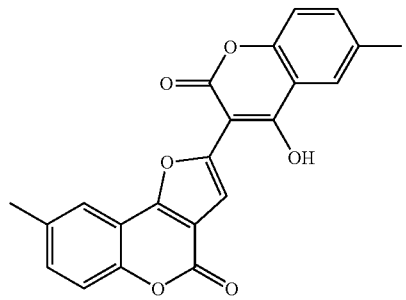

Example 2

2-Ethoxy-3-(4-hydroxy-6-methyl-2-oxo-2H-chromene-3-yl)-8-methyl-2,3-dihydro-4H-furo-[3,2-c]chromene-4-one (75 mg; 0.18 mmole) was suspended in acetic acid (5 mL). The reaction mixture was refluxed for 4 hours, whereat the starting material was dissolved, and then a yellow precipitate was formed. By cooling to room temperature a complete precipitation of a product occurred, whereupon the precipitate was filtered off, washed with acetic acid and diethylether, and dried. Obtained were 32 mg (47%) of the substance 2:

$^1$H-NMR (300 MHz, DMSO-$d_6$) δ/ppm: 2.40 (s, 3H); 2.44 (s, 3H); 7.25 (s, 1H); 7.30 (d, J=8.4 Hz, 1H); 7.44 (m, 2H) 7.50 (dd, J=8.6 Hz, J=2.0 Hz, 1H); 7.74 (bs, 1H); 7.82 (bs, 1H);

ES+ m/z (acetonitrile:water) [MH]+ 375.0.

Compound 3: 2-(4-Hydroxy-7-methyl-2-oxo-2H-chromene-3-yl)-7-methyl-4H-furo[3,2-c]chromene-4-one

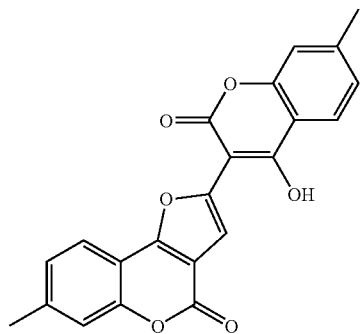

Example 3

2-Ethoxy-3-(4-hydroxy-7-methyl-2-oxo-2H-chromene-3-yl)-7-methyl-2,3-dihydro-4H-furo-[3,2-c]chromene-4-one (127 mg; 0.3 mmole) was suspended in acetic acid (5 mL). The reaction mixture was refluxed for 4 hours, whereat the starting material was dissolved, and then a yellow precipitate was formed. By cooling to room temperature a complete precipitation of a product occurred, whereupon the precipitate was filtered off, washed with acetic acid and diethylether, and dried. Obtained were 81 mg (63%) of the substance 3:
$^1$H-NMR (300 MHz, DMSO-$d_6$) δ/ppm: 2.44 (s, 3H); 2.45 (s, 3H); 7.21-7.32 (m, 4H); 7.41 (s, 1H); 7.83 (d, J=7.9 Hz, 1H); 7.93 (d, J=8.0 Hz, 1H);
ES− m/z (acetonitrile:water)[M-H]− 373.1.

Compound 4: 2-(4-Hydroxy-8-methyl-2-oxo-2H-chromene-3-yl)-6-methyl-4H-furo[3,2-c]chromene-4-one

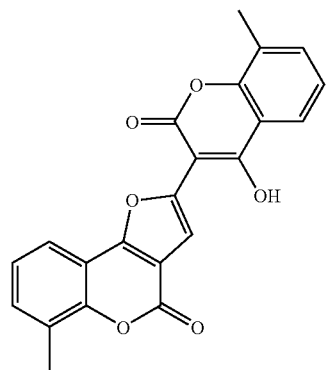

Example 4

2-Ethoxy-3-(4-hydroxy-8-methyl-2-oxo-2H-chromene-3-yl)-6-methyl-2,3-dihydro-4H-furo-[3,2-c]chromene-4-one (100 mg; 0.24 mmole) was suspended in acetic acid (5 mL). The reaction mixture was refluxed for 4 hours, whereat the starting material was dissolved, and then a yellow precipitate was formed. By cooling to room temperature a complete precipitation of a product occurred, whereupon the precipitate was filtered off, washed with acetic acid and diethylether, and dried. Obtained were 62 mg (69%) of the substance 4:

$^1$H-NMR (300 MHz, DMSO-$d_6$) δ/ppm: 2.39 (s, 3H); 2.45 (s, 3H); 7.27 (s, 1H); 7.29 (t, J=7.8 Hz, 1H); 7.35 (t, J=7.5 Hz, 1H); 7.51 (d, J=6.9 Hz, 1H); 7.57 (d, J=6.9 Hz, 1H); 7.77 (d, J=7.7 Hz, 1H); 7.78 (d, J=8.1 Hz, 1H);
ES+ m/z (acetonitrile:water) [MH]+ 375.0.

Compound 5: 8-Ethyl-2-(6-ethyl-4-hydroxy-2-oxo-2H-chromene-3-yl)-4H-furo[3,2-c]chromene-4-one

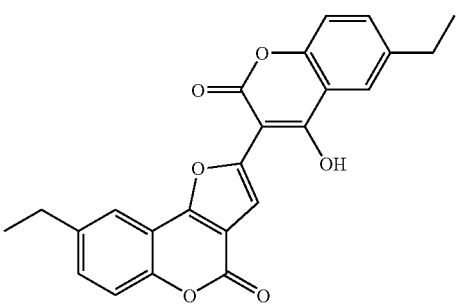

Example 5

8-Ethyl-3-(6-ethyl-4-hydroxy-2-oxo-2H-chromene-3-yl)-2-hydroxy-2,3-dihydro-4H-furo-[3,2-c]chromene-4-one (100 mg; 0.23 mmole) was suspended in acetic acid (3 mL). The reaction mixture was refluxed for 24 hours, whereat the starting material was dissolved, and then a yellow precipitate was formed. By cooling to room temperature a complete precipitation of a product occurred, whereupon the precipitate was filtered off, washed with acetic acid and diethylether and dried. Obtained were 40.8 mg (43%) of the substance 5:
$^1$H-NMR (300 MHz, DMSO-$d_6$) δ/ppm: 1.22 (t, J=7.5 Hz, 3H); 1.26 (t, J=7.6 Hz, 3H); 2.73 (m, 4H); 7.25 (s, 1H); 7.34 (d, J=8.4 Hz, 1H); 7.47 (m, 2H); 7.55 (dd, J=8.5 Hz, J=2.1 Hz, 1H); 7.74 (bs, 1H); 7.87 (d, J=2.0 Hz, 1H);
$^{13}$C-NMR (75.4 MHz, DMSO-$d_6$) δ/ppm: 15.4; 15.5; 27.4; 27.5; 94.9; 108.7; 111.1; 111.9; 115.8; 116.2; 116.8; 119.2; 122.4; 130.7; 133.1; 139.7; 140.5; 149.5; 150.2; 150.8; 155.9; 157.2; 160.1; 164.0;
ES+ m/z (acetonitrile:water) [MH]+ 402.8.

Compound 6: 6-Ethyl-2-(8-ethyl-4-hydroxy-2-oxo-2H-chromene-3-yl)-4H-furo[3,2-c]chromene-4-one

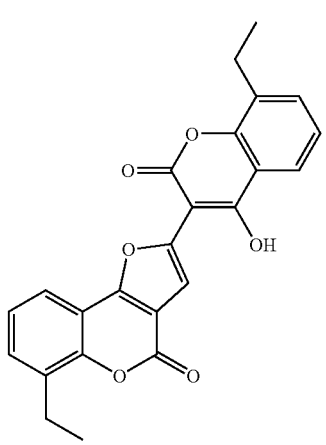

Example 6

6-Ethyl-3-(8-ethyl-4-hydroxy-2-oxo-2H-chromene-3-yl)-2-methoxy-2,3-dihydro-4H-furo[3,2-c]chromene-4-one (100 mg; 0.23 mmole) was suspended in acetic acid (5 mL). The reaction mixture was refluxed for 7 hours, whereat the starting material was dissolved, and then a yellow precipitate was formed. By cooling to room temperature a complete precipitation of a product occurred, whereupon the precipitate was filtered off, washed with acetic acid and diethylether, and dried. Obtained were 11.5 mg (12%) of the substance 6:

$^1$H-NMR (300 MHz, DMSO-$d_6$) δ/ppm: 1.25 (t, J=7.6 Hz, 3H); 1.27 (t, J=7.6 Hz, 3H); 2.81 (q, J=7.5 Hz, 2H); 2.87 (q, J=7.5 Hz, 2H); 7.28 (s, 1H); 7.33 (dd, J=7.6 Hz, J=7.8 Hz, 1H); 7.39 (dd, J=7.6 Hz, J=7.8 Hz, 1H); 7.52 (dd, J=7.5 Hz, J=1.3 Hz, 1H); 7.59 (dd, J=7.4 Hz, J=1.3 Hz, 1H); 7.79 (dd, J=7.7 Hz, J=1.5 Hz, 1H); 7.89 (dd, J=8.0 Hz, J=1.4 Hz, 1H);

$^{13}$C-NMR (75.4 MHz, DMSO-$d_6$) δ/ppm: 13.9; 14,0; 22.0; 22.4; 94.7; 108.6; 110.9; 111.9; 116.0; 118.6; 121.8; 123.8; 124.6; 130.4; 131.0; 131.7; 132.7; 149.6; 149.7; 150.3; 156.4; 157.0; 159.9; 164.3;

ES$^+$ m/z (acetonitrile:water) [MH]$^+$ 402.9.

Compound 7: 2-(4-Hydroxy-6-isopropyl-2-oxo-2H-chromene-3-yl)-8-isopropyl-4H-furo[3,2-c]chromene-4-one

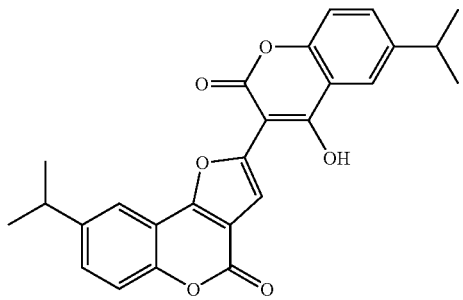

Example 7

3-(4-Hydroxy-6-isopropyl-2-oxo-2H-chromene-3-yl)-8-isopropyl-2-methoxy-2,3-dihydro-4H-furo[3,2-c]chromene-4-one (150 mg; 0.33 mmole) was suspended in acetic acid (5 mL). The reaction mixture was refluxed for 24 hours, whereat the starting material was dissolved, and then a yellow precipitate was formed. By cooling to room temperature a complete precipitation of a product occurred, whereupon the precipitate was filtered off, washed with acetic acid and diethylether, and dried. Obtained were 13 mg (14%) of the substance 7:

$^1$H-NMR (300 MHz, DMSO-$d_6$) δ/ppm: 1.27 (d, J=6.9 Hz, 6H); 1.28 (d, J=6.9 Hz, 6H); 3.05 (m, 2H); 7.27 (s, 1H); 7.36 (d, J=8.5 Hz, 1H); 7.49 (d, J=8.6 Hz, 1H); 7.55 (dd, J=8.6 Hz, J=2.0 Hz, 1H); 7.60 (dd, J=8.6 Hz, J=2.1 Hz, 1H); 7.77 (d, J=1.9 Hz, 1H); 7.92 (d, J=1.9 Hz, 1H);

$^{13}$C-NMR (75.4 MHz, DMSO-$d_6$) δ/ppm: 23.7; 23.8; 32.9; 32.9; 94.7; 108.3; 111.1; 111.9; 116.3; 116.9; 117.7; 121.1; 129.3; 131.7; 144.2; 145.1; 150.0; 150.2; 150.9; 155.8; 157.3; 160.3; 164.5;

ES$^+$ m/z (acetonitrile:water) [MH]$^+$ 431.0.

Compound 8: 2-(4-Hydroxy-8-isopropyl-2-oxo-2H-chromene-3-yl)-6-isopropyl-4H-furo[3,2-c]chromene-4-one

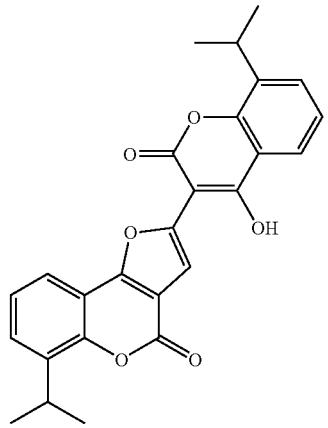

Example 8

3-(4-Hydroxy-8-isopropyl-2-oxo-2H-chromene-3-yl)-6-isopropyl-2-methoxy-2,3-dihydro-4H-furo[3,2-c]chromene-4-one (100 mg; 0.22 mmole) was suspended in acetic acid (2 mL). The reaction mixture was refluxed for 24 hours, whereat the starting material was dissolved, and then a yellow precipitate was formed. By cooling to room temperature a complete precipitation of a product occurred, whereupon the precipitate was filtered off, washed with acetic acid and diethylether, and dried. Obtained were 46 mg (49%) of the substance 8:

$^1$H-NMR (300 MHz, DMSO-$d_6$) δ/ppm: 1.30 (d, J=6.6 Hz, 6H); 1.31 (d, J=6.5 Hz, 6H); 3.52 (m, 2H); 7.29 (s, 1H); 7.37 (dd, J=7.8 Hz, J=7.8 Hz, 1H); 7.43 (dd, J=7.7 Hz, J=7.7 Hz, 1H); 7.58 (dd, J=7.6 Hz, J=1.3 Hz, 1H); 7.65 (dd, J=7.5 Hz, J=1.2 Hz, 1H); 7.80 (dd, J=7.7 Hz, J=1.5 Hz, 1H); 7.91 (dd, J=7.9 Hz, J=1.4 Hz, 1H);

$^{13}$C-NMR (75.4 MHz, DMSO-$d_6$) δ/ppm: 22.3; 26.2; 26.6; 94.7; 108.5; 110.9; 111.9; 116.1; 118.5; 121.8; 123.9; 124.7; 127.8; 130.1; 135.3; 136.1; 149.1; 149.6; 149.7; 156.4; 157.0; 160.0; 164.4;

ES$^+$ m/z (acetonitrile:water) [MH]$^+$ 430.8.

Compound 9: 2-(4-Hydroxy-5,7-dimethyl-2-oxo-2H-chromene-3-yl)-7,9-dimethyl-4H-furo[3,2-c]chromene-4-one

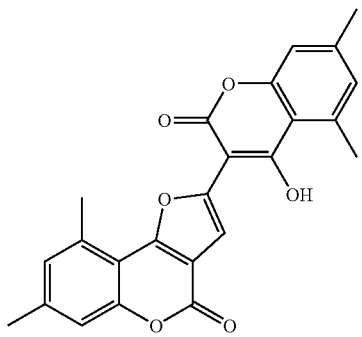

Example 9

3-(4-Hydroxy-5,7-dimethyl-2-oxo-2H-chromene-3-yl)-7,9-dimethyl-2-methoxy-2,3-dihydro-4H-furo[3,2-c]chromene-4-one (132 mg; 0.3 mmole) was suspended in acetic acid (5 mL). The reaction mixture was refluxed for 24 hours, whereat the starting material was dissolved, and then a yellow precipitate was formed. By cooling to room temperature a complete precipitation of a product occurred, whereupon the precipitate was filtered off, washed with acetic acid and diethylether, and dried. Obtained were 96 mg (78%) of the substance 9:

$^1$H-NMR (300 MHz, DMSO-$d_6$) δ/ppm: 2.37 (s, 3H); 2.40 (s, 3H); 2.70 (s, 3H); 2.71 (s, 3H); 7.00 (s, 1H); 7.06 (s, 1H); 7.10 (s, 1H) 7.18 (s, 1H); 7.21 (s, 1H);

$^{13}$C-NMR (75.4 MHz, DMSO-$d_6$) δ/ppm: 20.3; 20.8; 20.9; 23.1; 94.3; 108.1; 109.2; 110.5; 112.6; 114.7; 127.6; 128.7; 133.3; 137.7; 140.5; 142.9; 149.2; 152.6; 154.0; 157.0; 157.3; 159.9; 167.3;

ES$^+$ m/z (acetonitrile:water) [MH]$^+$ 403.2.

Compound 10: 2-(4-Hydroxy-6,7-dimethyl-2-oxo-2H-chromene-3-yl)-7,8-dimethyl-4H-furo[3,2-c]chromene-4-one

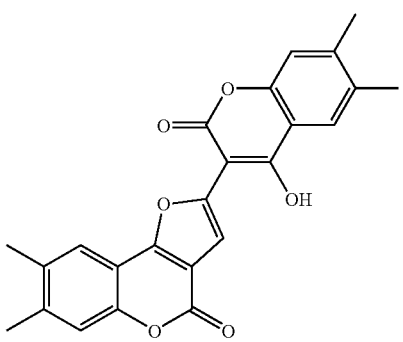

Example 10

2-Ethoxy-3-(4-hydroxy-6,7-dimethyl-2-oxo-2H-chromene-3-yl)-7,8-dimethyl-2,3-dihydro-4H-furo[3,2-c]chromene-4-one (100 mg; 0.22 mmole) was suspended in acetic acid (3 mL). The reaction mixture was refluxed for 3.5 hours, whereat the starting material was dissolved, and then a yellow precipitate was formed. By cooling to room temperature a complete precipitation of a product occurred, whereupon the precipitate was filtered off, washed with acetic acid and diethylether and dried. Obtained were 60 mg of a product, which upon recrystalization from acetic acid yielded 20 mg (20%) of the yellow powdery substance 10:

$^1$H-NMR (300 MHz, DMSO-$d_6$) δ/ppm: 2.31 (s, 3H); 2.34 (s, 6H); 2.36 (s, 3H); 7.20 (s, 1H); 7.22 (s, 1H); 7.38 (s, 1H); 7.69 (s, 1H); 7.77 (s, 1H);

ES$^-$ m/z (acetonitrile:water) [M-H]$^-$ 401.3.

Compound 11: 2-(4-Hydroxy-5,8-dimethyl-2-oxo-2H-chromene-3-yl)-6,9-dimethyl-4H-furo[3,2-c]chromene-4-one

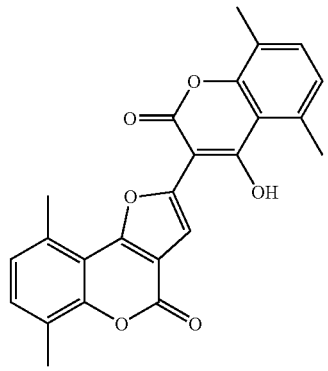

Example 11

2-Ethoxy-3-(4-hydroxy-5,8-dimethyl-2-oxo-2H-chromene-3-yl)-6,9-dimethyl-2,3-dihydro-4H-furo[3,2-c]chromene-4-one (134 mg; 0.3 mmole) was suspended in acetic acid (3 mL). The reaction mixture was refluxed for 2 hours, whereat the starting material was dissolved, and then a yellow precipitate was formed. By cooling to room temperature a complete precipitation of a product occurred, whereupon the precipitate was filtered off, washed with acetic acid and diethylether, and dried. Obtained were 85 mg (70%) of the substance 11:

$^1$H-NMR (300 MHz, DMSO-$d_6$) δ/ppm: 2.30 (s, 3H); 2.39 (s, 3H); 2.69 (s, 3H); 2.73 (s, 3H); 7.02 (d, J=7.8 Hz, 1H); 7.16 (d, J=7.8 Hz, 1H); 7.21 (s, 1H); 7.36 (d, J=7.9 Hz, 1H); 7.37 (d, J=7.6 Hz, 1H);

ES$^+$ m/z (acetonitrile:water) [MH]$^+$ 403.1.

Compound 12: 2-(4,5-Dihydroxy-2-oxo-2H-chromene-3-yl)-9-hydroxy-4H-furo[3,2-c]chromene-4-one

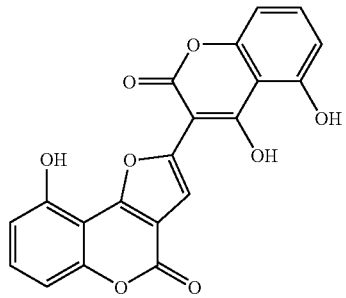

Example 12

4,5-Dihydroxycoumarin (100 mg; 0.56 mmole) was dissolved in methanol (3 mL), 2,2-dimethoxyacetaldehyde (2.8 mmole) was added and the reaction mixture was refluxed for 3 hours. By cooling to room temperature precipitation occurred, the precipitate was filtered off and washed with methanol. Obtained were 68 mg (61%) of the substance 12:

¹H-NMR (300 MHz, DMSO-d₆) δ/ppm: 6.54 (d, J=8.1 Hz, 1H); 6.86 (d, J=8.1, 1H); 6.64 (d, J=8.2 Hz, 1H); 6.95 (d, J=8.2 Hz, 1H); 7.03 (s, 1H); 7.13 (t, J=8.2 Hz, 1H); 7.36 (t, J=8.2, 1H); 8.0 (bs, 3H);

¹³C-NMR (75.4 MHz, DMSO-d₆) δ/ppm: 102.6; 104.4; 105.2; 106.1; 107.1; 109.2; 110.1; 110.7; 129.9; 132.1; 152.8; 152.8; 153.2; 153.5; 154.1; 157.6; 159.9; 160.9; 174.7;

ES⁻ m/z (acetonitrile:water) [M-H]⁻ 394.7.

Compound 13: 7,9-Dihydroxy-2-(4,5,7-trihydroxy-2-oxo-2H-chromene-3-yl)-4H-furo[3,2-c]chromene-4-one

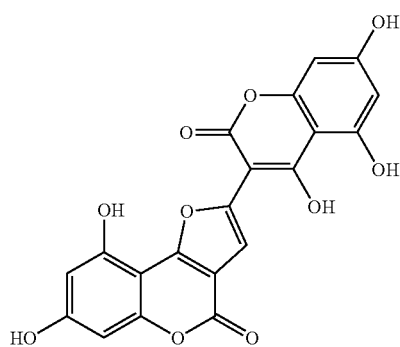

Example 13

2,7,9-Trihydroxy-3-(4,5,7-trihydroxy-2-oxo-2H-chromene-3-yl)-2,3-dihydro-4H-furo[3,2-c]chromene-4-one (600 mg; 1.4 mmole) was suspended in acetic acid (800 mL). The reaction mixture was heated to 80° C. during 15 minutes, whereat the starting material was dissolved, whereupon opacifying occurred. The reaction mixture was filtered off, the filtrate was evaporated to dryness and the residue was recrystallized from acetic acid (50%). Obtained were 155 mg (27%) of the substance 13 in the form of a greenish-brown amorphous precipitate.

¹H-NMR (500 MHz, DMSO-d₆) δ/ppm: 6.12 (d, J=2.2 Hz, 1H); 6.14 (d, J=2.1 Hz, 1H); 6.32 (d, J=2.1 Hz, 1H); 6.35 (d, J=2.1 Hz, 1H), 6.89 (s, 1H), 8.2 (bs, 3H);

¹³C-NMR (125.7 MHz, DMSO-d₆) δ/ppm: 88.6; 93.3; 94.1; 95.1; 97.1; 97.3; 98.4; 105.1; 106.4; 149.4; 153.8; 154.0; 154.6; 155.7; 157.3; 158.6; 159.5; 160.3; 161.5; 169.9;

ES⁻ m/z (acetonitrile:water) [M-H]⁻ 409.1.

Compound 14: 2-(4-Hydroxy-6-methoxy-2-oxo-2H-chromene-3-yl)-8-methoxy-4H-furo[3,2-c]chromene-4-one

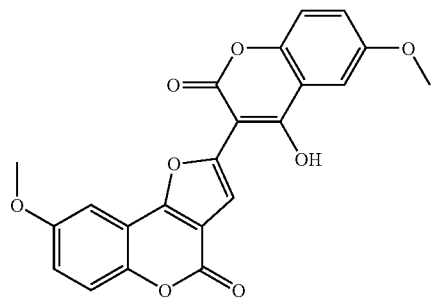

Example 14

2-Ethoxy-3-(4-hydroxy-6-methoxy-2-oxo-2H-chromene-3-yl)-8-methoxy-2,3-dihydro-4H-furo[3,2-c]chromene-4-one (124 mg; 0.27 mmole) was suspended in acetic acid (10 mL). The reaction mixture was refluxed for 6 hours, whereat the starting material was dissolved, and then a yellow precipitate was formed. By cooling to room temperature a complete precipitation occurred, the precipitate was filtered off, washed with acetic acid and diethylether, and dried. Obtained were 93 mg (85%) of the substance 14:

¹H-NMR (300 MHz, DMSO-d₆) δ/ppm: 3.86 (s, 3H); 3.88 (s, 3H); 7.20 (dd, J=8.9 Hz, J=3.0 Hz, 1H); 7.27 (s, 1H); 7.28 (dd, J=9.0 Hz, J=2.9 Hz, 1H); 7.35 (d, J=3.1 Hz, 1H); 7.37 (d, J=9.0 Hz, 1H); 7.48 (d, J=9.0 Hz, 1H); 7.79 (d, J=2.9 Hz, 1H);

ES⁺ (acetonitrile:water) [MH]⁺ 407.0.

Compound 15: 2-(4-Hydroxy-7-methoxy-2-oxo-2H-chromene-3-yl)-7-methoxy-4H-furo[3,2-c]chromene-4-one

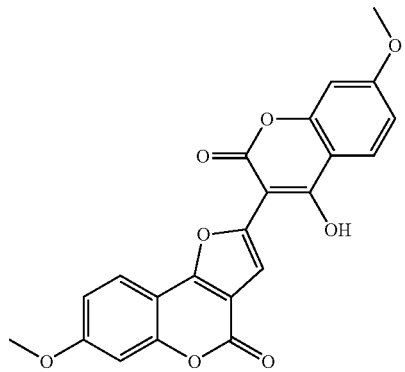

Example 15

2-Ethoxy-3-(4-hydroxy-7-methoxy-2-oxo-2H-chromene-3-yl)-7-methoxy-2,3-dihydro-4H-furo[3,2-c]chromene-4-one (67 mg; 0.15 mmole) was suspended in acetic acid (3 mL). The reaction mixture was refluxed for 5 hours, whereat the starting material was dissolved, and then a yellow precipitate was formed. By cooling to room temperature a complete precipitation occurred, the precipitate was filtered off, washed with acetic acid and diethylether, and dried. Obtained were 58 mg (97%) of the substance 15:

¹H-NMR (300 MHz, DMSO-d₆) δ/ppm: 3.89 (s, 6H); 7.00 (m, 2H); 7.07 (dd, J=8.5 Hz, J=2.4 Hz, 1H); 7.17 (s, 1H); 7.18 (d, J=2.3 Hz, 1H); 7.37 (d, J=9.0 Hz, 1H); 7.86 (d, J=8.6 Hz, 1H); 7.96 (d, J=8.4 Hz, 1H);

ES⁻ (acetonitrile:water) [M-H]⁻ 405.1.

Compound 16: 2-(4,7-Dihydroxy-5-methyl-2-oxo-2H-chromene-3-yl)-7-hydroxy-9-methyl-4H-furo[3,2-c]chromene-4-one

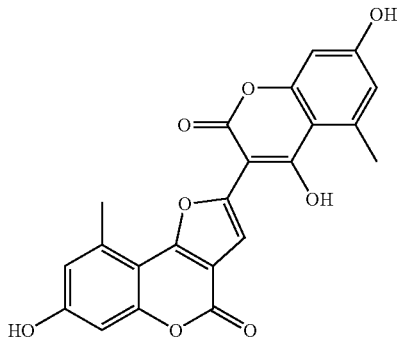

Example 16

3-(4,7-Dihydroxy-5-methyl-2-oxo-2H-chromene-3-yl)-7-hydroxy-9-methyl-2-methoxy-2,3-dihydro-4H-furo[3,2-c]chromene-4-one (100 mg; 0.22 mmole) was suspended in acetic acid (25 mL). The reaction mixture was refluxed for 40 hours, whereat the starting material was dissolved, and then a yellow precipitate was formed. By cooling to room temperature a complete precipitation occurred, the precipitate was filtered off, washed with acetic acid and diethylether, and dried. Obtained were 58 mg (63%) of the substance 16:

$^1$H-NMR (300 MHz, DMSO-$d_6$) δ/ppm: 2.50 (s, 3H); 2.66 (s, 3H); 6.58 (d, J=2.3 Hz, 1H); 6.63 (m, 1H); 6.73 (m, 2H); 7.089 (s, 1H); 10.44 (bs, 1H); 10.65 (bs, 1H);

ES$^-$ (acetonitrile:water) [M-H]$^-$ 405.0.

Compound 17: 8-Fluoro-2-(6-fluoro-4-hydroxy-2-oxo-2H-chromene-3-yl)-4H-furo[3,2-c]chromene-4-one

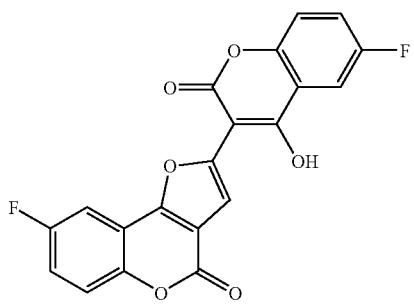

Example 17

2-Ethoxy-8-fluoro-3-(6-fluoro-4-hydroxy-2-oxo-2H-chromene-3-yl)-2,3-dihydro-4H-furo[3,2-c]chromene-4-one (75 mg; 0.18 mmole) was suspended in acetic acid (3 mL). The reaction mixture was refluxed for 4 hours, whereat the starting material was dissolved, and then a yellow precipitate was formed. By cooling to room temperature a complete precipitation occurred, the precipitate was filtered off, washed with acetic acid and diethylether, and dried. Obtained were 14 mg (21%) of the substance 17:

$^1$H-NMR (300 MHz, DMSO-$d_6$) δ/ppm: 7.30 (s, 1H); 7.40-7.54 (m, 3H); 7.62 (dd, J=9.2 Hz, J=4.5 Hz, 1H), 7.68-7.74 (m, 2H);

Compound 18: 2-(4-Hydroxy-6-chloro-2-oxo-2H-chromene-3-yl)-8-chloro-4H-furo[3,2-c]chromene-4-one

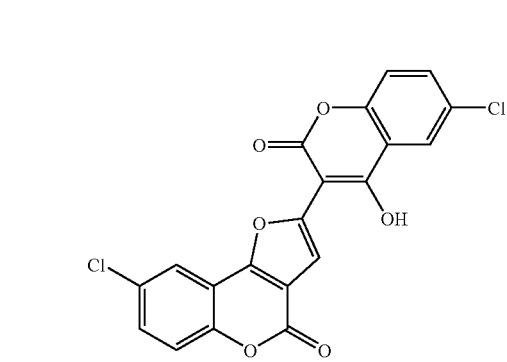

Example 18

2-Ethoxy-3-(4-hydroxy-6-chloro-2-oxo-2H-chromene-3-yl)-8-chloro-2,3-dihydro-4H-furo[3,2-c]chromene-4-one (230 mg; 0.5 mmole) was suspended in acetic acid (7 mL). The reaction mixture was refluxed for 5 hours, whereat the starting material was dissolved, and then a yellow precipitate was formed. By cooling to room temperature a complete precipitation occurred, the precipitate was filtered off, washed with acetic acid and diethylether, and dried. Obtained were 160 mg (77%) of the substance 18:

$^1$H-NMR (300 MHz, DMSO-$d_6$) δ/ppm: 7.28 (s, 1H); 7.37 (d, J=7.6 Hz, 1H); 7.52-7.67 (m, 3H); 7.82 (bd, 1H) 7.96 (bs, 1H);

ES$^+$ m/z (acetonitrile:water) [MH]$^+$ 414.9; 416.9; 418.9.

Compound 19: 8-Bromo-2-(6-bromo-4-hydroxy-2-oxo-2H-chromene-3-yl)-4H-furo[3 2-c]chromene-4-one

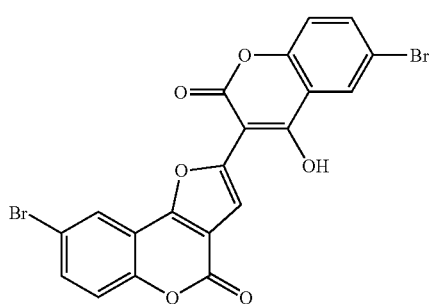

Example 19

8-Bromo-3-(6-bromo-4-hydroxy-2-oxo-2H-chromene-3-yl)-2-ethoxy-2,3-dihydro-4H-furo[3,2-c]chromene-4-one (90 mg; 0.16 mmole) was suspended in acetic acid (3 mL). The reaction mixture was refluxed for 3 hours, whereat the starting material was dissolved, and then a yellow precipitate was formed. By cooling to room temperature a complete precipitation occurred, the precipitate was filtered off, washed with acetic acid and diethylether, and dried. Obtained were 28 mg (34%) of the substance 19:

$^1$H-NMR (300 MHz, DMSO-$d_6$) δppm: 7.30 (d, J=8.7 Hz, 1H); 7.31 (s, 1H); 7.52 (d, J=8.7 Hz, 1H); 7.54 (m, 2H); 8.00 (d, J=2.2 Hz, 1H); 8.09 (d, J=2.3 Hz, 1H);

ES$^-$ m/z (acetonitrile:water) [M-H]$^-$ 501.0; 503.0; 505.0.

Compound 20: 2-(4-Hydroxy-7-chloro-2-oxo-2H-chromene-3-yl)-7-chloro-4H-furo[3,2-c]chromene-4-one

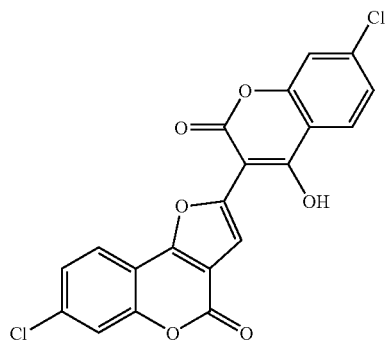

Example 20

2-Ethoxy-3-(4-hydroxy-7-chloro-2-oxo-2H-chromene-3-yl)-7-chloro-2,3-dihydro-4H-furo[3,2-c]chromene-4-one (124 mg; 0.27 mmole) was suspended in acetic acid (3 mL). The reaction mixture was refluxed for 5 hours, whereat the starting material was dissolved, and then a yellow precipitate was formed. By cooling to room temperature a complete precipitation occurred, the precipitate was filtered off, washed with acetic acid and diethylether, and dried. Obtained were 65 mg (57%) of the substance 20:

$^1$H-NMR (300 MHz, DMSO-$d_6$) δ/ppm: 7.28 (1H, s); 7.41 (1H, dd, J=2.0 Hz, J=8.5 Hz); 7.51 (1H, dd, J=1.9 Hz, J=8.4 Hz); 7.55 (1H, d, J=1.9 Hz); 7.75 (1H, d, J=1.8 Hz); 7.93 (1H, d, J=8.5 Hz) 8.00 (1H, d, J=8.5 Hz);

$^{13}$C-NMR (75.4 MHz, DMSO-$d_6$) δ/ppm: 94.9; 108.5; 111.7; 111.8; 116.6; 116.8; 117.7; 122.7; 124.8; 125.6; 126.4; 135.3; 137.8; 151.1; 152.6; 153.4; 155.4; 157.2; 160.2; 164,8;

ES$^-$ m/z (acetonitrile:water) [M-H]$^-$ 413.1; 415.1; 417.2.

Compound 21: 2-(4-Hydroxy-8-chloro-5-methyl-2-oxo-2H-chromene-3-yl)-6-chloro-9-methyl-4H-furo[3,2-c]chromene-4-one

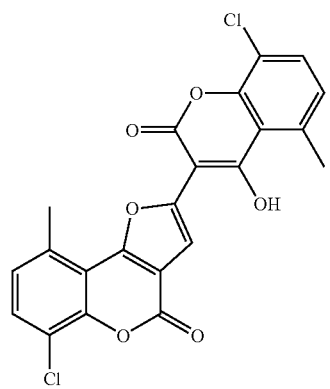

Example 21

3-(4-Hydroxy-8-chloro-5-methyl-2-oxo-2H-chromene-3-yl)-6-chloro-9-methyl-2-methoxy-2,3-dihydro-4H-furo[3,2-c]chromene-4-one (180 mg; 0.27 mmole) was suspended in acetic acid (5 mL). The reaction mixture was refluxed for 4 hours, whereat the starting material was dissolved, and then a yellow precipitate was formed. By cooling to room temperature a complete precipitation occurred, the precipitate was filtered off, washed with acetic acid and diethylether, and dried. Obtained were 33 mg (20%) of the substance 21:

$^1$H-NMR (300 MHz, DMSO-$d_6$) δ/ppm: 2.72 (s, 3H); 2.80 (s, 3H); 7.02 (d, J=8.2 Hz, 1H); 7.24 (d, J=8.7 Hz, 1H); 7.27 (s, 1H); 7.53 (d, J=8.1 Hz, 1H); 7.58 (d, J=8.1 Hz, 1H);

ES$^-$ m/z (acetonitrile:water) [M-H]$^-$ 440.9; 442.9; 444.8.

Compound 22: 2-(4-Hydroxy-6-chloro-7-methyl-2-oxo-2H-chromene-3-yl)-8-chloro-7-methyl-4H-furo[3,2-c]chromene-4-one

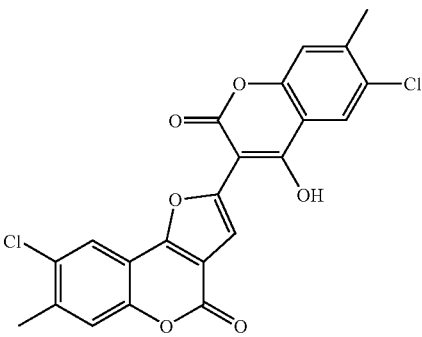

Example 22

3-(4-Hydroxy-6-chloro-7-methyl-2-oxo-2H-chromene-3-yl)-8-chloro-7-methyl-2-methoxy-2,3-dihydro-4H-furo[3,2-c]-chromene-4-one (100 mg; 0.21 mmole) was suspended in acetic acid (5 mL). The reaction mixture was refluxed for 8 hours, whereat the starting material was dissolved, and then a yellow precipitate was formed. By cooling to room temperature a complete precipitation occurred, the precipitate was filtered off, washed with acetic acid and diethylether, and dried. Obtained were 40 mg (43%) of the substance 22:

ES$^+$ m/z (acetonitrile:water) [MH]$^+$ 442.9; 444.9; 446.8.

Compound 23: 2-(1-Hydroxy-3-oxo-3H-benzo[f]chromene-2-yl)-4H-benzo[f]furo[3,2:c]chromene-4-one

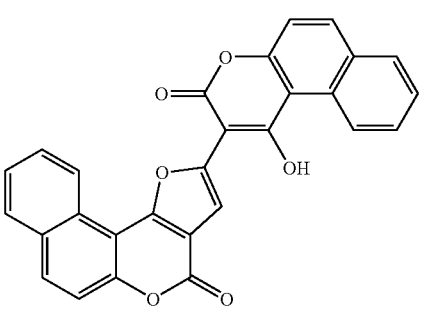

Example 23

2-Ethoxy-3-(1-hydroxy-3-oxo-3H-benzo[f]chromene-2-yl)-2,3-dihydro-4H-benzo[f]furo[3,2-c]chromene-4-one (52 mg, 0.1 mmole) was suspended in acetic acid (3 mL). The reaction mixture was refluxed for 2.5 hours, whereat the starting material was dissolved, and then a yellow precipitate was formed. By cooling to room temperature a complete precipitation occurred, the precipitate was filtered off, washed with acetic acid and diethylether, and dried. Obtained were 32 mg (69%) of the substance 23:

$^1$H-NMR (300 MHz, DMSO-$d_6$) δ/ppm: 7.47 (s, 1H); 7.54 (d, J=5.4 Hz, 1H); 7.60 (m, 1H); 7.66-7.73 (m, 1H); 7.80-7.86 (m, 1H); 8.02 (d, J=7.9 Hz, 1H); 8.10-8.19 (m, 3H); 9.27 (d, J=8.6 Hz, 1H); 9.83 (d, J=8.6 Hz, 1H);

ES$^-$ m/z (acetonitrile:water) [M-H]$^-$ 445.1.

Compound 24: Sodium salt of 2-(4-hydroxy-2-oxo-2H-chromene-3-yl)-4H-furo-[3,2-c]chromene-4-one

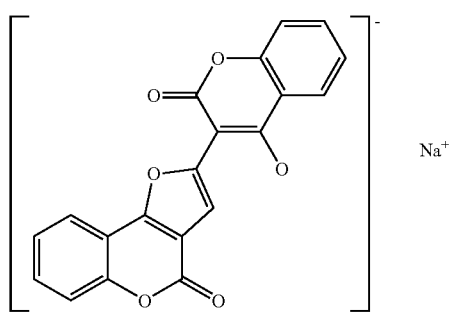

Example 24

2-(4-Hydroxy-2-oxo-2H-chromene-3-yl)-4H-furo[3,2-c]chromene-4-one (173 mg; 0.5 mmole) was suspended in a mixture of acetonitrile (5 mL) and an aqueous sodium hydroxide solution (1 mL) (22 mg; 0.55 mmole). The reaction mixture was stirred at room temperature until the complete starting coumarin was dissolved. Then the solvent was evaporated at a reduced pressure and the obtained solid was recrystallized from a mixture of ethanol and diethyl ether. Obtained were 131 mg (71%) of the yellow powdery water-soluble substance 24:

$^1$H-NMR (300 MHz, DMSO-$d_6$) δ/ppm: 7.24 (s, 1H); 7.25-7.31 (m, 2H); 7.38-7.57 (m, 4H); 8.08-8.14 (m, 2H);

$^{13}$C-NMR (75 MHz, MeOH-$d_4$) δ/ppm: 93.7; 105.8; 113.0; 114.6; 117.4; 118.0; 122.4; 123.6; 124.5; 126.0; 126.5; 131.1; 132.2; 153.4; 155.0; 156.7; 157.1; 161.2; 166.8; 176.6.

Compound 25: 7-Ethyl-2-(7-ethyl-4-hydroxy-2-oxo-2H-chromene-3-yl)-4H-furo[3,2-c]chromene-4-one

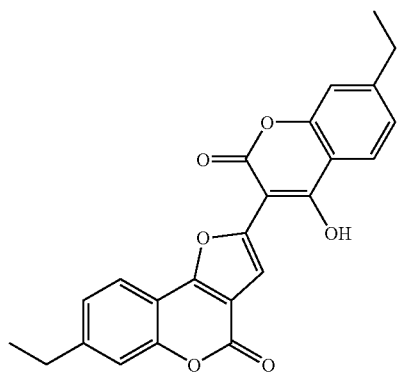

Example 25

7-Ethyl-3-(7-ethyl-4-hydroxy-2-oxo-2H-chromene-3-yl)-2-methoxy-2,3-dihydro-4H-furo[3,2-c]chromene-4-one (100 mg; 0.23 mmole) was suspended in acetic acid (5 mL). The reaction mixture was refluxed for 5 hours, whereat the starting material was dissolved, and then a yellow precipitate was formed. By cooling to room temperature a complete precipitation of the product occurred, whereupon the precipitate was filtered off, washed with acetic acid and diethylether, and dried. Obtained were 24 mg (26%) of the substance 25:

$^1$H-NMR (300 MHz, DMSO-$d_6$) δ/ppm: 1.25 (t, J=7.3 Hz, 6H); 2.75 (m, 4H); 7.24 (s, 1H); 7.28 (d, J=7.8 Hz, 1H); 7.29 (s, 1H); 7.33 (d, J=8.2 Hz, 1H); 7.43 (s, 1H); 7.86 (d, J=8.0 Hz, J=1.5 Hz, 1H); 7.96 (d, J=8.5 Hz, 1H);

$^{13}$C-NMR (75.4 MHz, DMSO-$d_6$) δ/ppm: 15.1; 15.2; 28.2; 28.3; 108.4; 110.0; 110.5; 114.2; 115.3; 116.0; 120.8; 124.2; 124.2; 124.9; 147.9; 149.7; 150.4; 152.2; 152.8; 156.2; 157.4; 160.4; 164.5;

ES$^+$ m/z (acetonitrile:water) [MH]$^+$ 403.1.

Compound 26: 2-(4,6-Dihydroxy-2-oxo-2H-chromene-3-yl)-8-hydroxy-4H-furo[3,2-c]chromene-4-one

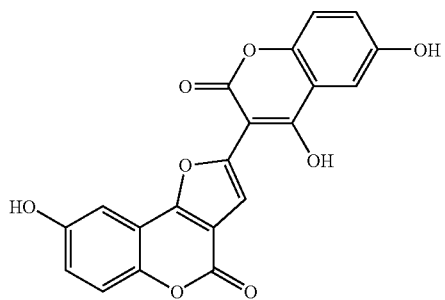

Example 26

3-(4,6-Dihydroxy-2-oxo-2H-chromene-3-yl)-8-hydroxy-2-methoxy-2,3-dihydro-4H-furo[3,2-c]chromene-4-one (90 mg; 0.22 mmole) was suspended in acetic acid (12 mL). The reaction mixture was refluxed for 20 hours, whereat the starting material was dissolved, and then a yellow precipitate was formed. By cooling to room temperature a complete precipitation of the product occurred, whereupon the precipitate was filtered off, washed with acetic acid and diethylether, and dried. Obtained were 35 mg (42%) of the substance 26:

$^1$H-NMR (300 MHz, DMSO-$d_6$) δ/ppm: 7.04 (dd, J=9.0 Hz, J=2.9 Hz, 1H); 7.13 (dd, J=8.9 Hz, J=2.9 Hz, 1H); 7.23 (d, J=2.8 Hz, 1H); 7.25 (s, 1H); 7.29 (d, J=8.9 Hz, 1H); 7.38 (d, J=2.8 Hz, 1H); 7.42 (d, J=9.0, 1H); 10.0 (bs, 2H);

ES$^-$ m/z (acetonitrile:water) [M-H]$^-$ 377.0.

Compound 27: 2-(4,7-Dihydroxy-2-oxo-2H-chromene-3-yl)-7-hydroxy-4H-furo[3,2-c]chromene-4-one

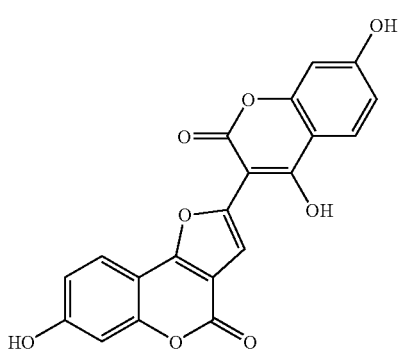

Example 27

3-(4,6-Dihydroxy-2-oxo-2H-chromene-3-yl)-8-hydroxy-2-methoxy-2,3-dihydro-4H-furo[3,2-c]chromene-4-one (90 mg; 0.22 mmole) was suspended in acetic acid (5 mL). The reaction mixture was refluxed for 5 hours, whereat the starting material was dissolved, and then a yellow precipitate was formed. By cooling to room temperature a complete precipitation of the product occurred, whereupon the precipitate was filtered off, washed with acetic acid and diethylether, and dried. Obtained were 51 mg (62%) of the substance 27:

$^1$H-NMR (300 MHz, DMSO-$d_6$) δ/ppm: 6.75 (d, J=2.2 Hz, 1H); 6.85 (dd, J=8.8 Hz, J=2.3 Hz, 1H); 6.89 (s, 1H); 6.89-6.93 (m, 1H); 7.13 (s, 1H); 7.78 (d, J=8.6 Hz, 1H); 7.88 (d, J=8.8 Hz, 1H); 10.60 (bs, 1H); 10.79 (bs, 1H);

$^{13}$C-NMR (75.4 MHz, DMSO-$d_6$) δ/ppm: 92.5; 102.0; 103.0; 104.5; 107.8; 108.4; 113.2; 113.6; 122.3; 125.8; 124.9; 148.3; 153.9; 154.6; 157.2; 157.6; 160.4; 160.7; 162.5; 164.2;

ES$^-$ m/z (acetonitrile:water) [M-H]$^-$ 377.1.

Compound 28: 2-(4-Hydroxy-8-methoxy-2-oxo-2H-chromene-3-yl)-6-methoxy-4H-furo[3,2-c]chromene-4-one

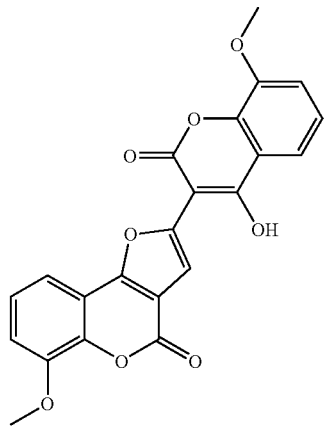

Example 28

3-(4-Hydroxy-8-methoxy-2-oxo-2H-chromene-3-yl)-2,6-dimethoxy-2,3-dihydro-4H-furo[3,2-c]chromene-4-one (100 mg; 0.23 mmole) was suspended in acetic acid (40 mL). The reaction mixture was refluxed for 24 hours, whereat the starting material was dissolved, and then a yellow precipitate was formed. By cooling to room temperature a complete precipitation occurred, the precipitate was filtered off, washed with acetic acid and diethylether, and dried. Obtained were 67 mg (72%) of the substance 28:

$^1$H-NMR (300 MHz, DMSO-$d_6$) δ/ppm: 3.94 (s, 3H); 3.96 (s, 3H); 7.26 (s, 1H); 7.34 (m, 4H); 7.50 (dd, J=7.7 Hz, J=1.3 Hz, 1H); 7.62 (dd, J=7.4 Hz, J=1.8 Hz, 1H);

$^{13}$C-NMR (75.4 MHz, DMSO-$d_6$) δ/ppm: 56.0; 56.1; 94.8; 108.1; 111.0; 111.9; 112.7; 113.3; 115.0; 115.3; 117.0; 123.5; 124.6; 141.3; 142.3; 146.5; 147.0; 149.8; 155.8; 156.6; 159.4; 164.1;

ES$^+$ (acetonitrile:water) [MH]$^+$ 405.1.

Compound 29: 2-(4-Hydroxy-2-oxo-2H-benzo[g]chromene-3-yl)-4H-benzo[g]furo[3.2-c]chromene-4-one

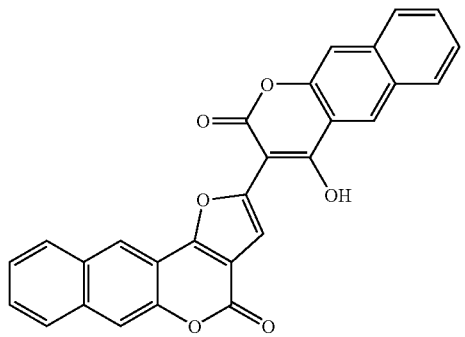

Example 29

3-(4-Hydroxy-2-oxo-2H-benzo[g]chromene-3-yl)-2-methoxy-2,3-dihydro-4H-benzo[g]furo[3,2-c]chromene-4-one (100 mg, 0.2 mmole) was suspended in acetic acid (5mL). The reaction mixture was refluxed for 5 hours, whereat the starting material was dissolved, and then a yellow precipitate was formed. By cooling to room temperature a complete precipitation occurred, the precipitate was filtered off, washed with acetic acid and diethylether, and dried. Obtained were 70.7 mg (76%) of the substance 29:

$^1$H-NMR (300 MHz, DMSO-$d_6$) δ/ppm: 7.34 (s, 1H); 7.52-7.68 (m, 4H); 7.90 (s, 1H); 8.01 (d, J=3.2 Hz, 1H); 8.04 (s, 1H); 8.05 (bs, 1H); 8.11 (d, J=8.0 Hz, 1H); 8.20 (d, J=7.9 Hz, 1H); 8.57 (s, 1H); 8.70 (s, 1H);

$^{13}$C-NMR (75.4 MHz, DMSO-$d_6$) δ/ppm: 95.1; 108.7; 109.0; 111.9; 112.0; 112.9; 116.9; 120.4; 125.3; 125.7; 126.2; 127.2; 127.6; 127.9; 128.4; 128.6; 129.0; 129.3; 129.8; 133.5; 135.0; 148.8; 150.4; 155.5; 157.3; 160.3; 164.2;

ES$^+$ m/z (acetonitrile:water) [MH]$^+$ 446.9.

Compound 30: 2-(4-Hydroxy-6,8-dichloro-2-oxo-2H-chromene-3-yl)-6,8-dichloro-4H-furo[3,2-c]chromene-4-one

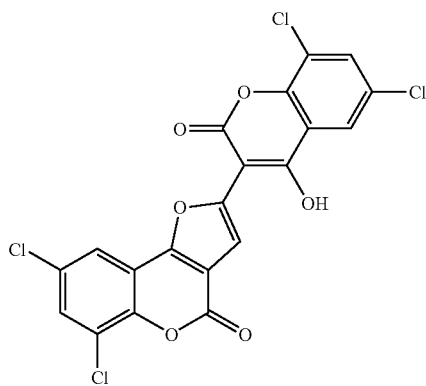

Example 30

3-(4-Hydroxy-6,8-dichloro-2-oxo-2H-chromene-3-yl)-6,8-dichloro-2-dimethoxy-2,3-dihydro-4H-furo[3,2-c]chromene-4-one (100 mg; 0.19 mmole) was suspended in acetic acid (15 mL). The reaction mixture was refluxed for 7 hours, whereat the starting material was dissolved, and then a yellow precipitate was formed. By cooling to room temperature a complete precipitation occurred, the precipitate was filtered off, washed with acetic acid and diethylether, and dried. Obtained were 46 mg (49%) of the substance 30:

$^1$H-NMR (300 MHz, DMSO-$d_6$) δ/ppm: 7.29 (s, 1H); 7.76 (d, J=2.4 Hz, 1H); 7.79-7.82 (m, 2H); 7.84 (d, J=2.4 Hz, 1H);

$^{13}$C-NMR (75.4 MHz, DMSO-$d_6$) δ/ppm: 91.9; 104.7; 112.6; 114.6; 118.3; 120.7; 121.6; 122.5; 122.9; 126.9; 128.6; 129.0; 130.9; 145.6; 147.3; 151.9; 155.0; 155.9; 159.2; 167.0;

ES$^+$ (acetonitrile:water) [MH]$^+$ 484.1.

Compound 31: 2-(4-Hydroxy-7,8-dimethyl-2-oxo-2H-chromene-3-yl)-6,7-dimethyl-4H-furo[3,2-c]chromene-4-one

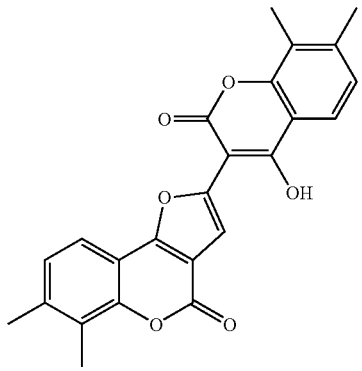

Example 31

3-(4-Hydroxy-7,8-dimethyl-2-oxo-2H-chromene-3-yl)-6,7-dimethyl-2-methoxy-2,3-dihydro-4H-furo[3,2-c]chromene-4-one (100 mg; 0.24 mmole) was suspended in acetic acid (5 mL). The reaction mixture was refluxed for 18 hours, whereat the starting material was dissolved, and then a yellow precipitate was formed. By cooling to room temperature a complete precipitation of the product occurred, whereupon the precipitate was filtered off, washed with acetic acid and diethylether, and dried. Obtained were 60 mg (65%) of the substance 31:

$^1$H-NMR (300 MHz, DMSO-$d_6$) δ/ppm: 2.30 (s, 3H); 2.38 (s, 3H); 2.40 (s, 3H); 2.43 (s, 3H); 7.20 (d, J=7.8 Hz, 1H); 7.23 (s, 1H); 7.29 (d, J=7.8 Hz, 1H); 7.68 (d, J=7.9 Hz, 1H); 7.79 (d, J=7.6 Hz, 1H);

ES$^+$ m/z (acetonitrile:water) [ME]$^+$ 403.1.

Compound 32: 2-(4-Hydroxy-6,8-dimethyl-2-oxo-2H-chromene-3-yl)-6,8-dimethyl-4H-furo[3,2-c]chromene-4-one

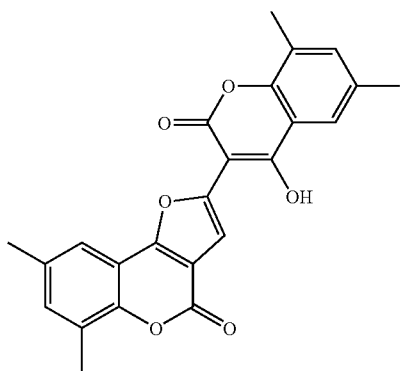

Example 32

3-(4-Hydroxy-6,8-dimethyl-2-oxo-2H-chromene-3-yl)-6,8-dimethyl-2-methoxy-2,3-dihydro-4H-furo[3,2-c]

chromene-4-one (105 mg; 0.24 mmole) was suspended in acetic acid (5 mL). The reaction mixture was refluxed for 5 hours, whereat the starting material was dissolved, and then a yellow precipitate was formed. By cooling to room temperature a complete precipitation of the product occurred, whereupon the precipitate was filtered off, washed with acetic acid and diethylether, and dried. Obtained were 90 mg (90%) of the substance 32:

$^1$H-NMR (300 MHz, DMSO-$d_6$) δ/ppm: 2.35 (s, 3H); 2.36 (s, 3H); 2.41 (s, 6H); 7.23 (s, 1H); 7.31 (s, 1H); 7.37 (s, 1H); 7.55 (s, 1H); 7.61 (s, 1H);

$^{13}$C-NMR (75.4 MHz, DMSO-$d_6$) δ/ppm: 15.0; 15.4; 20.2; 20.3; 94.6; 108.6; 110.8; 111.5; 115.6; 118.0; 121.1; 124.8; 125.5; 132.6; 132.9; 133.6; 135.1; 148.3; 148.9; 149.6; 156.3; 157.1; 160.1; 164.2;

Preparation of the Starting Compounds

Method A

P-1: 2-Ethoxy-3-(4-hydroxy-6-methyl-2-oxo-2H-chromene-3-yl)-8-methyl-2,3-dihydro-4H-furo[3,2-c]chromene-4-one 4-Hydroxy-6-methylcoumarin (88 mg, 0.5 mmole) was dissolved in ethanol (3 mL). A 40% aqueous gyloxal solution (287 μL, 2.5 mmole) was added and the reaction mixture was refluxed for 3 hours. By cooling to room temperature a white precipitate was precipitated, which was filtered off and washed with ethanol. Obtained was the title compound in a 70% yield and of sufficient purity to be used the next synthesis step:

$^1$H-NMR (300 MHz, DMSO-$d_6$) δ/ppm: 1.22 (t, J=7.0 Hz, 3H); 2.38 (s, 3H); 2.42 (s, 3H); 3.81 (m, 1H); 3.98 (m, 1H); 4.84 (d, J=2.6 Hz, 1H); 6.16 (d, J=3.6 Hz, 1H); 7.28 (d, J=8.4 Hz, 1H); 7.46 (dd, J=8.3 Hz, J=1.3 Hz, 1H); 7.51 (dd, J=8.4 Hz, J=1.6 Hz, 1H); 7.58 (s, 1H); 7.82 (s, 1H); 12.01 (bs, 1H);

ES$^-$ m/z (acetonitrile:water) [M-H]$^-$ 419.1;

Starting from a corresponding coumarin and according to the process described under Method A with slight changes in molar ratios, temperature and/or the duration of the reaction, there were prepared the following compounds:

P-2: 2-Ethoxy-3-(4-hydroxy-7-methyl-2-oxo-2H-chromene-3-yl)-7-methyl-2,3-dihydro-4H-furo[3,2-c]chromene-4-one in a 86% yield:

$^1$H-NMR (300 MHz, DMSO-$d_6$) δ/ppm: 1.22 (t, J=7.0 Hz, 3H); 2.41 (s, 3H); 2.44 (s, 3H); 3.84 (m, 1H); 3.97 (m, 1H); 4.80 (m, 1H); 6.15 (d, J=3.5 Hz, 1H); 7.22-7.32 (m, 4H); 7.67 (d, J=8.0 Hz, 1H); 7.89 (d, J=8.6 Hz, 1H); 11.22 (bs, 1H);

ES$^-$ m/z (acetonitrile:water) [M-H]$^-$ 419.1;

P-3: 2-Ethoxy-3-(4-hydroxy-8-methyl-2-oxo-2H-chromene-3-yl)-6-methyl-2,3-dihydro-4H-furo[3,2-c]chromene-4-one in a 56% yield:

$^1$H-NMR (300 MHz, DMSO-$d_6$) δ/ppm: 1.22 (t, J=7.1 Hz, 3H); 2.32 (s, 3H); 2.37 (s, 3H); 3.82 (m, 1H); 3.98 (m, 1H); 4.83 (m, 1H); 6.12 (d, J=3.5 Hz, 1H); 7.26 (m, 1H); 7.32 (t, J=7.6 Hz, 1H); 7.47 (m, 1H); 7.57 (d, J=7.3 Hz, 1H); 7.62 (d, J=8.1 Hz, 1H); 7.82 (m, 1H);

ES$^+$ m/z (acetonitrile:water) [MH]$^+$ 421.5;

P-4: 2-Ethoxy-3-(4-hydroxy-6,7-dimethyl-2-oxo-2H-chromene-3-yl)-7,8-dimethyl-2,3-dihydro-4H-furo[3,2-c]chromene-4-one in a 56% yield:

$^1$H-NMR (300 MHz, DMSO-$d_6$) δ/ppm: 1.21 (t, J=7.0 Hz, 3H); 2.28 (s, 3H); 2.31 (s, 6H); 2.34 (s, 3H); 3.81 (m, 1H); 3.98 (m, 1H); 4.80 (d, J=3.0 Hz, 1H); 6.12 (d, J=3.4 Hz, 1H); 7.19 (s, 1H); 7.27 (s, 1H); 7.53 (s, 1H); 7.76 (s, 1H); 11.99 (bs, 1H);

ES$^+$ m/z (acetonitrile:water) [MH]$^+$ 449.1;

P-5: 2-Ethoxy-3-(4-hydroxy-5,8-dimethyl-2-oxo-2H-chromene-3-yl)-6,9-dimethyl-2,3-dihydro-4H-furo[3,2-c]chromene-4-one in a 61% yield:

$^1$H-NMR (300 MHz, DMSO-$d_6$) δ/ppm: 1.24 (t, J=7.1 Hz, 3H); 2.25 (s, 3H); 2.31 (s, 3H); 2.66 (s, 3H); 2.72 (s, 3H) 3.81 (m, 1H); 3.95 (m, 1H); 4.91 (d, J=2.7 Hz, 1H); 6.13 (d, J=3.0 Hz, 1H); 7.05 (d, J=7.7 Hz, 1H); 7.11 (d, J=7.9 Hz, 1H); 7.35 (d, J=7.6 Hz, 1H); 7.42 (d, J=7.8 Hz, 1H); 11.99 (bs, 1H);

P-6: 2-Ethoxy-3-(4,6-dihydroxy-2-oxo-2H-chromene-3-yl)-8-hydroxy-2,3-dihydro-4H-furo[3,2:c]chromene-4-one in a 87% yield:

$^1$H-NMR (300 MHz, DMSO-$d_6$) δ/ppm: 1.22 (t, J=7.1 Hz, 3H); 3.80 (m, 1H); 3.96 (m, 1H); 4.81 (d, J=2.5 Hz, 1H); 6.13 (d, J=3.4 Hz, 1H); 7.04-7.34 (m, 6H, Ar); 9.79 (bs, 1H); 9.93 (bs, 1H) 11.9 (bs, 1H);

ES$^-$ m/z (acetonitrile:water) [M-H]$^-$ 423.2;

P-7: 3-(4,7-Dihydroxy-8-methyl-2-oxo-2H-chromene-3-yl)-2-ethoxy-7-hydroxy-6-methyl-2,3-dihydro-4H-furo[3,2-c]chromene-4-one in a 51% yield:

$^1$H-NMR (300 MHz, DMSO-$d_6$) δ/ppm: 1.21 (t, J=7.0 Hz, 3H); 2.12 (s, 3H); 2.15 (s, 3H); 3.78 (dq, J=7.0 Hz, J=9.7 Hz, 1H); 3.98 (dq, J=7.0, J=9.7 Hz, 1H); 4.73 (d, J=3.3 Hz, 1H); 6.07 (d, J=3.3 Hz, 1H); 6.84 (d, J=8.7 Hz, 1H); 6.90 (d, J=8.5, 1H); 7.46 (d, J=8.7 Hz, 1H); 7.69 (d, J=7.8 Hz, 1H); 10.4 (s, 1H); 10.5 (s, 1H); 11.0 (bs, 1H);

ES$^-$ m/z (acetonitrile:water) [M-H]$^-$ 450.9;

P-8: 2-Ethoxy-3-(4-hydroxy-6-methoxy-2-oxo-2H-chromene-3-yl)-8-methoxy-2,3-dihydro-4H-furo[3,2-c]chromene-4-one in a 68% yield:

$^1$H-NMR (300 MHz, DMSO-$d_6$) δ/ppm: 1.23 (t, J=7.1 Hz, 3H); 3.76 (s, 3H); 3.78 (s, 3H); 3.87 (m, 1H); 4.01 (m, 1H); 4.84 (bs, 1H); 6.17 (d, J=3.5 Hz, 1H); 7.19 (d, J=2.9 Hz, 1H); 7.24 (dd, J=9.0 Hz, J=2.9 Hz, 1H); 7.29 (dd, J=9.1 Hz, J=3.0 Hz, 1H); 7.35 (d, J=9.0 Hz, 1H); 7.42 (d, J=9.1 Hz, 1H); 7.54 (d, J=2.9 Hz, 1H); 12.0 (bs, 1H);

P-9: 2-Ethoxy-3-(4-hydroxy-7-methoxy-2-oxo-2H-chromene-3-yl)-7-methoxy-2,3-dihydro-4H-furo[3,2-c]chromene-4-one in a 68% yield:

$^1$H-NMR (300 MHz, DMSO-$d_6$) δ/ppm: 1.22 (t, J=7.0 Hz, 3H); 3.80 (m, 1H); 3.83 (s, 3H); 3.85 (s, 3H); 3.87 (m, 1H); 4.75 (d, J=2.5 Hz, 1H); 6.12 (d, J=3.2 Hz, 1H); 6.97-7.06 (m, 3H); 7.07 (d, J=2.3 Hz, 1H); 7.69 (d, J=8.8 Hz, 1H); 7.92 (d, J=9.7 Hz, 1H); 11.9 (bs, 1H);

ES$^-$ m/z (acetonitrile:water) [M-H]$^-$ 451.2;

P-10: 2-Ethoxy-3-(4-hydroxy-8-methoxy-2-oxo-2H-chromene-3-yl)-6-methoxy-2,3-dihydro-4H-furo[3,2-c]chromene-4-one in a 40% yield:

$^1$H-NMR (300 MHz, DMSO-$d_6$) δ/ppm: 1.22 (3H, t, J=7.1 Hz); 3.81 (1H, m); 3.89 (3H, s); 3.91 (3H, s); 3.98 (1H, m); 4.84 (1H, d, J=2.3 Hz); 6.17 (1H, d, J=3.5 Hz); 7.28-7.39 (4H, m); 7.56 (1H, d, J=6.2 Hz); 7.57 (1H, d, J=6.2 Hz);

ES$^+$ m/z (acetonitrile:water) [MH]$^+$ 453.5;

P-11: 2-Ethoxy-8-fluoro-3-(6-fluoro-4-hydroxy-2-oxo-2H-chromene-3-yl)-2,3-dihydro-4H-furo[3,2-c]chromene-4-one in a 39% yield:

$^1$H-NMR (300 MHz, DMSO-$d_6$) δ/ppm: 1.22 (3H, t, J=7.1 Hz); 3.82 (1H, m); 4.00 (1H, m); 4.86 (1H, bs); 6.20 (1H, d, J=3.4 Hz); 7.43-7.63 (5H, m); 7.79 (1H, dd, J=9.0 Hz, J=2.9 Hz);

ES$^-$ m/z (acetonitrile:water) [M-H]$^-$ 426.8;

P-12: 2-Ethoxy-3-(4-hydroxy-6-chloro-2-oxo-2H-chromene-3-yl)-8-chloro-2,3-dihydro-4H-furo[3,2-c]chromene-4-one in a 79% yield:

$^1$H-NMR (300 MHz, DMSO-$d_6$) δ/ppm: 1.23 (3H, t, J=7.0 Hz); 3.83 (1H, m); 4.01 (1H, m); 4.86 (1H, bs); 6.21 (1H, d, J=3.5 Hz); 7.45 (1H, d, J=8.8 Hz); 7.53 (1H, d, J=8.9 Hz); 7.70 (1H, dd, J=8.8 Hz, J=2.4 Hz); 7.75 (1H, dd, J=8.9 Hz, J=2.6 Hz); 7.82 (1H, d, J=2.5 Hz); 8.05 (1H, d, J=2.5 Hz);

P-13: 8-Bromo-3-(6-bromo-4-hydroxy-2-oxo-2H-chromene-3-yl)-2-ethoxy-2,3-dihydro-4H-furo[3,2-c]chromene-4-one in a 67% yield:

$^1$H-NMR (300 MHz, DMSO-$d_6$) δ/ppm: 1.22 (3H, t, J=7.1 Hz); 3.83 (1H, m); 4.01 (1H, m); 4.86 (1H, bs); 6.19 (1H, d, J=3.5 Hz); 7.39 (1H, d, J=8.8 Hz); 7.46 (1H, d, J=8.9 Hz); 7.81 (1H, dd, J=8.9 Hz, J=2.4 Hz); 7.87 (1H, dd, J=8.8 Hz, J=2.5 Hz); 7.94 (1H, d, J=2.3 Hz); 8.18 (1H, d, J=2.3 Hz);

ES$^-$ m/z (acetonitrile:water) [M-H]$^-$ 547.2; 549.2; 551.2;

P-14: 2-Ethoxy-3-(4-hydroxy-7-chloro-2-oxo-2H-chromene-3-yl)-7-chloro-2,3-dihydro-4H-furo[3,2-c]chromene-4-one in a 56% yield:

$^1$H-NMR (300 MHz, DMSO-$d_6$) δ/ppm: 1.22 (t, J=7.0 Hz, 3H); 3.82 (m, 1H); 3.98 (m, 1H); 4.84 (bs, 1H); 6.20 (d, J=3.4 Hz, 1H); 7.48 (m, 2H); 7.60 (d, J=1.8 Hz, 1H); 7.69 (d, J=1.6 Hz, 1H); 7.81 (d, J=8.5 Hz, 1H); 8.01 (d, J=8.6 Hz, 1H);

ES$^-$ m/z (acetonitrile:water) [M-H]$^-$ 459.1; 461.1; 463.2;

P-15: 2-Ethoxy-3-(1-hydroxy-3-oxo-3H-benzo[]chromene-2-yl)-2,3-dihydro-4H-benzo[f]furo[3,2-c]chromene-4-one in a 82% yield:

$^1$H-NMR (300 MHz, DMSO-$d_6$) δ/ppm: 1.31 (t, J=7.1 Hz, 3H); 3.96 (dq, J=9.7 Hz, J=7.1 Hz, 1H); 4.14 (dq, J=9.7 Hz, J=7.1 Hz, 1H); 5.14 (d, J=3.4 Hz, 1H); 6.38 (d, J=3.4 Hz, 1H); 7.53 (d, J=8.9 Hz, 1H); 7.62 (m, 1H); 7.63 (d, J=8.9 Hz, 1H); 7.69-7.77 (m, 2H); 7.83 (m, 1H); 8.07 (dd, J=7.9 Hz, J=1.5 Hz, 1H); 8.13 (dd, J=7.8 Hz, J=1.5 Hz, 1H); 8.20 (d, J=8.9 Hz, 1H); 8.28 (d, J=9.1 Hz, 1H); 9.00 (d, J=8.3 Hz, 1H); 9.48 (d, 8.7 Hz, 1H);

MS m/z: ES$^+$ (acetonitrile:water) [MH]$^+$: 493.4;

P-16: 2-Ethoxy-3-(4-hydroxy-2-oxo-2H-benzo[g]chromene-3-yl)-2,3-dihydro-4H-benzo[r]furo[3,2-c]chromene-4-one in a 67% yield:

$^1$H-NMR (300 MHz, DMSO-$d_6$) δ ppm: 1.27 (t, J=7.1 Hz, 3H); 3.89 (dq, J=9.7 Hz, J=7.1 Hz, 1H); 4.07 (dq, J=9.6 Hz, J=7.1 Hz, 1H); 4.99 (bs, 1H); 6.31 (d, J=3.5 Hz, 1H); 7.53-7.70 (m, 4H); 7.91 (s, 1H); 7.99 (s, 1H); 8.00-8.10 (m, 2H); 8.21 (d, J=8.1 Hz, 1H); 8.50 (s, 1H); 8.67 (s, 1H);

MS m/z: ES$^-$ (acetonitrile:water) [M-H]$^-$: 491.4;

P-17: 2-Ethoxy-3-(4,7-dihydroxy-2-oxo-2H-benzo[g]chromene-2-yl)-2,9-dihydroxy-2,3-dihydro-4H-benzo[g]furo[3,2-c]chromene-4-one in a 85% yield:

$^1$H-NMR (300 MHz, DMSO-$d_6$) δ/ppm: 1.26 (t, J=7.0 Hz, 3H); 3.87 (m, 1H); 4.05 (m, 1H); 4.95 (bs, 1H); 6.25 (d, J=3.4 Hz, 1H); 7.23-7.28 (m, 4H); 7.37 (d, J=2.0 Hz, 1H); 7.78 (s, 1H); 7.86-7.91 (m, 3H); 8.23 (s, 1H); 8.40 (s, 1H); 9.90 (bs, 1H); 9.94 (bs, 1H), 12.00 (bs, 1H);

Method B

P-18: 3-(4,7-Dihydroxy-5-methyl-2-oxo-2H-chromene-3-yl)-7-hydroxy-9-methyl-2-methoxy-2,3-dihydro-4H-furo[3,2-c]chromene-4-one 4,7-Dihydroxy-5-methylcoumarin (200 mg; 1.04 mmole) was dissolved in methanol (5 mL). A 60% aqueous dimethoxyacetaldehyde solution (792 μL; 8.7 mmole) was added and the reaction mixture was refluxed for 5 hours. By cooling to room temperature a white precipitate was precipitated, which was filtered off and washed with methanol. Obtained was the title compound in a 92% yield and of sufficient purity to be used in the next synthesis step:

$^1$H-NMR (300 MHz, DMSO-$d_6$) δ/ppm: 2.61 (s, 3H); 2.66 (s, 3H); 3.17 (s, 3H); 4.79 (d, J=3.4 Hz, 1H); 5.95 (d, J=3.3 Hz, 1H); 6.50 (d, J=2.4 Hz, 1H); 6.59 (d, J=2.1 Hz, 2H); 6.63 (d, J=2.8 Hz, 1H); 10.4 (s, 1H); 10.5 (s, 1H); 11.0 (bs, 1H);

$^{13}$C-NMR (75.4 MHz, DMSO-$d_6$) δ/ppm: 20.8; 23.6; 42.5; 56.3; 96.9; 98.5; 100.0; 100.4; 103.5; 107.1; 113.9; 115.1; 115.3; 116.1; 137.2; 139.0; 155.4; 157.5; 158.4; 160.0; 162.4; 165.0; 166.7

ES$^-$ m/z: (acetonitrile:water) [M-H]$^-$: 438.9;

Starting from a corresponding coumarin and according to the process described under Method B with slight changes in molar ratios, temperature and/or the duration of the reaction, there were prepared the following compounds:

P-19: 8-Ethyl-3-(6-ethyl-4-hydroxy-2-oxo-2H-chromene-3-yl)-2-methoxy-2,3-dihydro-4H-furo[3,2-c]chromene-4-one in a 38% yield:

$^1$H-NMR (300 MHz, DMSO-$d_6$) δ/ppm: 1.22 (t, J=7.5 Hz, 6H); 2.68 (q, J=7.5 Hz, 4H); 3.62 (s, 3H); 4.86 (d, J=2.7 Hz, 1H); 6.10 (d, J=3.4 Hz, 1H); 7.31 (d, J=8.4 Hz, 1H); 7.39 (d, J=8.5 Hz, 1H); 7.51 (dd, J=8.5 Hz, J=2.0 Hz, 1H); 7.56 (dd, J=8.5 Hz, J=2.1 Hz, 1H); 7.62 (d, J=1.9 Hz, 1H); 7.87 (d, J=1.7 Hz, 1H); 11.99 (bs, 1H);

$^{13}$C-NMR (75.4 MHz, DMSO-$d_6$) δ/ppm: 15.5; 15.6; 27.3; 27.5; 42.5; 56.6; 100.7; 102.0; 111.7; 114.6; 115.5; 116.1; 116.5; 120.9; 122.0; 132.2; 132.7; 139.6; 140.1; 150.4; 152.8; 158.3; 161.5; 162.0; 165.0;

ES$^+$ m/z (acetonitrile:water) [MH]$^+$ 434.9;

P-20: 6-Ethyl-3-(8-ethyl-4-hydroxy-2-oxo-2H-chromene-3-yl)-2-methoxy-2,3-dihydro-4H-furo[3,2-c]chromene-4-one in a 58% yield:

$^1$H-NMR (300 MHz, DMSO-$d_6$) δ/ppm: 1.21 (m, 6H); 2.77 (m, 4H); 3.61 (s, 3H); 4.88 (d, J=3.4 Hz, 1H); 6.12 (d, J=3.4 Hz, 1H); 7.32 (dd, J=7.7 Hz, J=7.5 Hz, 1H); 7.37 (dd, J=7.7 Hz, J=7.4 Hz, 1H); 7.54 (d, J=6.5 Hz, 1H); 7.60 (d, J=6.5 Hz, 1H); 7.64 (dd, J=7.8 Hz, J=1.5 Hz, 1H); 7.88 (dd, J=7.8 Hz, J=1.1 Hz, 1H); 11.99 (bs, 1H);

$^{13}$C-NMR (75.4 MHz, DMSO-$d_6$,) δ/ppm: 14.0; 22.0; 22.3; 42.5; 56.5; 100.6; 101.9; 111.7; 114.6; 115.7; 120.4; 121.3; 123.7; 124.1; 131.0; 131.5; 132.0; 132.4; 150.0; 152.3; 158.1; 162.3; 165.4;

ES$^+$ m/z (acetonitrile:water) [MH]$^+$ 435.0;

P-21: 3-(4-Hydroxy-6-isopropyl-2-oxo-2H-chromene-3-yl)-8-isopropyl-2-methoxy-2,3-dihydro-4H-furo[3,2-c]chromene-4-one in a 28% yield:

$^1$H-NMR (300 MHz, DMSO-$d_6$) δ/ppm: 1.26 (m, 12H); 3.01 (m, 2H); 3.62 (s, 3H); 4.85 (bs, 1H); 6.10 (d, J=3.4 Hz, 1H); 7.32 (d, J=8.5 Hz, 1H); 7.40 (d, J=9.2 Hz, 1H); 7.54 (dd, J=8.5 Hz, J=1.8 Hz, 1H); 7.61 (m, 2H); 7.91 (d, J=1.7 Hz, 1H); 11.99 (bs, 1H);

$^{13}$C-NMR (75.4 MHz, DMSO-$d_6$,) δ/ppm: 23.7; 23.8; 32.8; 33.0; 42.5; 56.6; 102.1; 111.6; 114.7; 115.5; 116.2; 116.6; 119.4; 120.5; 131.0; 131.4; 144.2; 144.7; 150.4; 152.9; 158.3; 162.1; 165.0;

ES$^+$ m/z (acetonitrile:water) [MH]$^+$ 463.0;

P-22: 3-(4-Hydroxy-8-isopropyl-2-oxo-2H-chromene-3-yl)-6-isopropyl-2-methoxy-2,3-dihydro-4H-furo[3,2-c]chromene-4-one in a 29% yield:

$^1$H-NMR (300 MHz, DMSO-$d_6$) δ/ppm: 1.25 (m, 6H); 3.42 (m, 4H); 3.61 (s, 3H); 4.88 (d, J=3.1 Hz, 1H); 6.12 (d, J=3.4 Hz, 1H); 7.35 (dd, J=7.8 Hz, J=7.5 Hz, 1H); 7.40 (dd, J=7.5 Hz, J=7.8 Hz, 1H); 7.59 (dd, J=7.6 Hz, J=1.2 Hz, 1H); 7.65 (dd, J=7.8 Hz, J=1.5 Hz, 1H); 7.66 (dd, J=7.6 Hz, J=1.5 Hz, 1H); 7.88 (dd, J=8.0 Hz, J=1.3 Hz, 1H); 11.99 (bs, 1H);

$^{13}$C-NMR (75.4 MHz, DMSO-$d_6$) δ/ppm: 22.3; 22.4; 26.2; 26.5; 42.5; 56.5; 101.8; 111.7; 114.6; 115.7; 120.3; 121.1; 123.8; 124.2; 129.3; 129.7; 135.3; 135.8; 149.3; 151.7; 158.1; 162.3; 165.5;

ES$^-$ m/z (acetonitrile:water) [M-H]$^-$ 461.0;

P-23: 3-(4-Hydroxy-6,8-dimethyl-2-oxo-2H-chromene-3-yl)-6,8-dimethyl-2-methoxy-2,3-dihydro-4H-furo[3,2-c]chromene-4-one in a 80% yield:

$^1$H-NMR (300 MHz, DMSO-$d_6$) δ/ppm: 2.30 (s, 3H); 2.33 (s, 3H); 2.35 (s, 3H); 2.38 (s, 3H); 3.60 (s, 3H); 4.86 (d, J=3.1 Hz, 1H); 6.07 (d, J=3.4 Hz, 1H); 7.35 (s, 1H); 7.40 (s, 1H); 7.44 (s, 1H); 7.66 (s, 1H);

$^{13}$C-NMR (75.4 MHz, DMSO-$d_6$) δ/ppm: 15.1; 15.4; 20.2; 20.5; 42.6; 56.6; 100.6; 101.9; 111.5; 114.7; 115.4; 119.9; 120.9; 124.9; 125.4; 132.6; 133.3; 134.4; 134.9; 148.7; 151.1; 158.3; 161.5; 162.2; 165.4;

ES$^+$ m/z: (acetonitrile:water) [MH]$^+$: 434.9;

P-24: 6,8-Dichloro-3-(6,8-dichloro-4-hydroxy-2-oxo-2H-chromene-3-yl)-2-methoxy-2,3-dihydro-4H-furo[3,2-c]chromene-4-one in a 90% yield:

$^1$H-NMR (300 MHz, DMSO-$d_6$) δ/ppm: 3.62 (s, 3H); 4.90 (bs, 1H); 6.16 (d, J=3.4 Hz, 1H); 7.83 (d, J=2.3 Hz, 1H); 7.99 (m, 2H); 8.05 (d, J=2.3 Hz, 1H);

$^{13}$C-NMR (75.4 MHz, DMSO-$d_6$) δ/ppm: 42.4; 56.6; 101.0; 103.5; 114.2; 115.0; 119.0; 121.0; 121.2; 121.6; 122.2; 127.9; 128.4; 131.6; 132.2; 146.8; 148.8; 156.6; 161.5; 163.8;

P-25: 6,8-Dibromo-3-(6,8-dibromo-4-hydroxy-2-oxo-2H-chromene-3-yl)-2-methoxy-2,3-dihydro-4H-furo[3,2-c]chromene-4-one in a 44% yield:

$^1$H-NMR (300 MHz, DMSO-$d_6$) δ/ppm: 3.62 (s, 3H); 4.89 (bs, 1H); 6.14 (d, J=3.4 Hz, 1H); 7.97 (d, J=2.3 Hz, 1H); 8.15 (d, J=2.3 Hz, 1H); 8.17 (d, J=2.3 Hz, 1H); 8.25 (d, J=2.3 Hz, 1H);

$^{13}$C-NMR (75.4 MHz, DMSO-$d_6$) δ/ppm: 42.4; 56.6; 100.8; 103.5; 110.5; 110.9; 114.5; 115.1; 115.8; 116.3; 119.4; 124.4; 125.8; 136.9; 137.6; 148.2; 150.3; 156.7; 161.0; 163.7;

ES$^-$ m/z (acetonitrile:water) [M-H]$^-$ 688.4; 690.4; 692.4; 694.4; 696.4;

P-26: 6,8,9-Trichloro-3-(4-hydroxy-5,6,8-trichloro-2-oxo-2H-chromene-3-yl)-2-methoxy-2,3-dihydro-4H-furo[3,2-c]chromene-4-one in a 42% yield:

$^1$H-NMR (300 MHz, DMSO-$d_6$) δ/ppm: 3.59 (s, 3H); 4.88 (bs, 1H); 6.03 (d, J=3.3 Hz, 1H); 8.11 (s, 1H); 8.26 (s, 1H);

$^{13}$C-NMR (75.4 MHz, DMSO-$d_6$) δ/ppm: 42.5; 57.1; 107.0; 114.1; 115.6; 120.5; 121.0; 126.5; 128.2; 129.0; 131.8; 132.8; 149.3; 150.3; 156.4; 163.5;

ES$^-$ m/z (acetonitrile:water) [M-H]$^-$ 581.4; 583.4; 585.4; 587.4; 589.4;

P-27: 3-(4-Hydroxy-8-chloro-5-methyl-2-oxo-2H-chromene-3-yl)-6-chloro-9-methyl-2-methoxy-2,3-dihydro-4H-furo[3,2-c]chromene-4-one in a 73% yield:

$^1$H-NMR (300 MHz, DMSO-$d_6$) δ/ppm: 2.70 (s, 3H); 2.74 (s, 3H); 3.59 (s, 3H); 4.96 (d, J=3.5 Hz, 1H); 6.09 (d, J=3.5 Hz, 1H); 7.15 (d, J=8.2 Hz, 1H); 7.23 (d, J=8.2 Hz, 1H); 7.64 (d, J=8.2 Hz, 1H); 7.72 (d, J=8.2 Hz, 1H);

$^{13}$C-NMR (75.4 MHz, DMSO-$d_6$) δ/ppm: 20.5; 23.3; 41.5; 56.5; 99.8; 102.7; 112.8; 114.3; 117.8; 118.0; 127.0; 127.8; 131.2; 132.0; 135.0; 136.7; 148.6; 150.4; 156.9; 159.9; 166.1;

ES$^+$ m/z (acetonitrile:water) [MH]$^+$ 474.7; 476.7; 478.8;

P-28: 3-(4-Hydroxy-6-chloro-7-methyl-2-oxo-2H-chromene-3-yl)-8-chloro-7-methyl-2-methoxy-2,3-dihydro-4H-furo[3,2-c]chromene-4-one in a 97% yield:

$^1$H-NMR (300 MHz, DMSO-$d_6$) δ/ppm: 2.40 (s, 3H); 2.44 (s, 3H); 3.61 (s, 3H); 4.84 (d, J=2.3 Hz, 1H); 6.10 (d, J=3.3 Hz, 1H); 7.45 (s, 1H); 7.52 (s, 1H); 7.78 (s, 1H); 8.03 (s, 1H);

$^{13}$C-NMR (75.4 MHz, DMSO-$d_6$,) δ/ppm: 19.8; 20.1; 42.5; 56.6; 100.3; 102.1; 111.0; 114.7; 115.2; 118.6; 119.0; 121.9; 123.1; 128.7; 129.0; 140.6; 141.1; 150.6; 152.9; 157.8; 161.1; 164.0;

ES$^+$ m/z (acetonitrile:water) [MH]$^+$ 474.7; 476.7; 478.8;

P-29: 3-(4,5-Dihydroxy-2-oxo-2H-chromene-3-yl)-9-hydroxy-2-methoxy-2,3-dihydro-4H-furo[3,2-c]chromene-4-one in a 57% yield:

$^1$H-NMR (300 MHz, DMSO-$d_6$) δ/ppm: 3.53 (s, 3H); 4.54 (d, J=3.4 Hz, 1H); 5.89 (d, J=3.5 Hz, 1H); 6.66 (d, J=8.0 Hz, 1H); 6.75 (d, J=7.6 Hz, 1H); 6.79 (d, J=8.5 Hz, s, 1H); 6.82 (d, J=8.5 Hz, 1H); 7.37 (t, J=8.1 Hz, 1H); 7.42 (t, J=8.1 Hz, 1H); 10.5 (bs, 1H);

$^{13}$C-NMR (75.4 MHz, DMSO-$d_6$) δ/ppm: 42.5; 56.2; 96.9; 101.0; 102.0; 104.4; 106.8; 106.9; 109.7; 110.5; 114.3; 132.3; 132.7; 153.3; 154.9; 155.9; 156.4; 158.2; 165.5; 167.0;

ES$^+$ m/z (acetonitrile:water) [MH]$^+$ 410.8;

P-30: 3-(4-Hydroxy-6,8-diisopropyl-2-oxo-2H-chromene-3-yl)-6,8-diisopropyl-2-methoxy-2,3-dihydro-4H-furo[3,2-c]chromene-4-one in a 34% yield:

$^1$H-NMR (300 MHz, DMSO-$d_6$) δ/ppm: 1.23-1.31 (m, 24H); 2.98 (m, 2H); 3.49-3.59 (m, 2H); 3.68 (s, 3H); 4.54 (d, J=1.7 Hz, 1H); 6.70 (d, J=1.7 Hz, 1H); 7.29 (d, J=2.0 Hz, 1H); 7.38 (d, J=2.0 Hz, 1H); 7.55 (d, J=2.0 Hz, 1H); 7.69 (d, J=2.0 Hz, 1H);

ES$^-$ m/z (acetonitrile:water) [M-H]$^-$: 545.2;

P-31: 3-(4-Hydroxy-6-methyl-2-oxo-2H-chromene-3-yl)-8-methyl-2-methoxy-2,3-dihydro-4H-furo[3,2-c]chromene-4-one in a 76% yield:

$^1$H-NMR (300 MHz, DMSO-$d_6$) δ/ppm: 2.40 (s, 3H); 2.44 (s, 3H); 3.62 (s, 3H); 4.86 (d, J=3.3 Hz, 1H); 6.10 (d, J=3.4 Hz, 1H); 7.30 (d, J=8.4 Hz, 1H); 7.38 (d, J=8.5 Hz, 1H); 7.48 (dd, J=8.5 Hz, J=1.7 Hz, 1H); 7.54 (dd, J=8.7 Hz, J=2.0 Hz, 1H); 7.61 (s, 1H); 7.83 (s, 1H); 11.80-12.20 (bs, 1H);

$^{13}$C-NMR (75.4 MHz, DMSO-$d_6$) δ/ppm: 20.1; 20.4; 42.5; 56.5; 100.7; 102.0; 111.6; 114.5; 116.0; 116.4; 122.1; 123.1; 133.2; 133.7; 133.8; 150.3; 152.6; 158.3; 161.5; 161.9; 164.1;

ES$^+$ m/z: (acetonitrile:water) [MH]$^+$: 407.1;

P-32: 3-(4-Hydroxy-7-methyl-2-oxo-2H-chromene-3-yl)-7-methyl-2-methoxy-2,3-dihydro-4H-furo[3,2-c]chromene-4-one in a 70% yield:

$^1$H-NMR (300 MHz, DMSO-$d_6$) δ/ppm: 2.41 (s, 3H); 2.45 (s, 3H); 3.60 (s, 3H); 4.83 (d, J=3.1 Hz, 1H); 6.08 (d, J=3.4 Hz, 1H); 7.23 (dd, J=7.0 Hz, J=7.1 Hz, 2H); 7.30 (d, J=7.8 Hz, 2H); 7.69 (d, J=7.9 Hz, 1H); 7.90 (d, J=7.6 Hz, 1H);

¹³C-NMR (75.4 MHz, DMSO-d₆) δ/ppm: 21.1; 21.3; 42.5; 56.6; 100.1; 101.3; 109.5; 113.4; 114.7; 116.3; 116.7; 122.4; 125.1; 125.5; 143.3; 143.9; 152.3; 154.7; 158.4; 161.6; 162.2; 165.2;

ES⁺ m/z: (acetonitrile:water) [MH]⁺: 407.1.

P-33: 3-(4-Hydroxy-8-methyl-2-oxo-2H-chromene-3-yl)-6-methyl-2-methoxy-2,3-dihydro-4H-furo[3,2-c]chromene-4-one in a 84% yield:

¹H-NMR (300 MHz, DMSO-d₆) δ/ppm: 2.35 (s, 3H); 2.38 (s, 3H); 3.61 (s, 3H); 4.88 (d, J=3.2 Hz, 1H); 6.11 (d, J=3.5 Hz, 1H); 7.26-7.36 (m, 2H); 7.53 (d, J=7.0 Hz, 1H); 7.56 (d, J=6.9 Hz, 1H); 7.65 (d, J=7.3 Hz, 1H); 7.86 (d, J=7.3 Hz, 1H);

¹³C-NMR (75.4 MHz, DMSO-d₆) δ/ppm: 15.2; 15.5; 42.6; 56.6; 100.7; 102.0; 111.7; 114.8; 115.7; 120.4; 121.3; 123.3; 123.9; 125.2; 125.7; 133.4; 133.8; 150.5; 152.9; 158.2; 162.3; 165.4;

ES⁻ m/z: (acetonitrile:water) [M-H]⁻: 405.2;

P-34: 3-(7-Ethyl-4-hydroxy-2-oxo-2H-chromene-3-yl)-7-ethyl-2-methoxy-2,3-dihydro-4H-furo[3,2-c]chromene-4-one in a 53% yield:

¹H-NMR (300 MHz, DMSO-d₆) δ/ppm: 1.21 (t, J=7.6 Hz, 3H); 1.22 (t, J=7.6 Hz, 3H); 2.67-2.77 (m, 4H); 3.61 (s, 3H); 4.84 (d, J=2.8 Hz, 1H); 6.08 (d, J=3.4 Hz, 1H); 7.25 (s, 1H); 7.28 (d, J=6.4 Hz, 1H); 7.30 (d, J=8.0 Hz, 1H); 7.33 (s, 1H); 7.72 (d, J=7.9 Hz, 1H); 7.93 (d, J=8.0 Hz, 1H);

¹³C-NMR (75.4 MHz, DMSO-d₆) δ/ppm: 15.1; 15.2; 28.1; 28.4; 42.5; 56.6; 100.2; 101.3; 109.8; 113.7; 114.7; 115.2; 115.6; 122.6; 123.5; 124.0; 124.4; 149.5; 150.0; 152.4; 154.8; 158.4; 161.6; 162.2; 165.2;

ES⁺ m/z: (acetonitrile:water) [MH]⁺: 435.1;

P-35: 3-(4-Hydroxy-5,7-dimethyl-2-oxo-2H-chromene-3-yl)-7,9-dimethyl-2-methoxy-2,3-dihydro-4H-furo[3,2-c]chromene-4-one in a 61% yield:

¹H-NMR (300 MHz, DMSO-d₆) δ/ppm: 2.33 (s, 3H); 2.37 (s, 3H); 2.67 (s, 1H); 2.71 (s, 1H); 3.58 (s, 3H); 4.88 (d, J=3.4 Hz, 1H); 6.02 (d, J=3.4 Hz, 1H); 6.99 (s, 2H); 7.02 (s, 2H); 7.05 (s, 1H); 7.11 (s, 1H); 12.0 (bs, 1H);

¹³C-NMR (75.4 MHz, DMSO-d₆) δ/ppm: 20.5; 20.7; 21.0; 23.3; 41.5; 56.4; 99.0; 101.2; 108.8; 112.4; 113.9; 114.5; 127.6; 128.8; 135.2; 137.0; 141.9; 142.8; 153.6; 155.6; 158.2; 160.8; 164.6; 166.4;

ES⁺ m/z: (acetonitrile:water) [MH]⁺: 435.0;

P-36: 3-(4-Hydroxy-5,8-dimethyl-2-oxo-2H-chromene-3-yl)-6,9-dimethyl-2-methoxy-2,3-dihydro-4H-furo[3,2-c]chromene-4-one in a 87% yield:

¹H-NMR (300 MHz, DMSO-d₆) δ/ppm: 2.26 (s, 3H); 2.31 (s, 3H); 2.68 (s, 3H); 2.72 (s, 3H); 3.59 (s, 3H); 4.94 (d, J=3.4 Hz, 1H); 6.05 (d, J=3.4 Hz, 1H); 7.05 (d, J=7.8 Hz, 1H); 7.11 (d, J=7.8 Hz, 1H); 7.35 (d, J=7.7 Hz, 1H); 7.43 (d, J=7.8 Hz, 1H);

¹³C-NMR (75.4 MHz, DMSO-d₆) δ/ppm: 15.2; 15.4; 20.6; 23.4; 41.5; 56.4; 99.7; 102.0; 111.0; 114.0; 114.7; 122.8; 123.1; 125.9; 127.0; 132.3; 133.0; 133.1; 134.7; 151.6; 153.6; 158.0; 160.6; 164.9; 166.7;

ES⁺ m/z: (acetonitrile:water) [MH]⁺: 434.9;

P-37: 3-(4-Hydroxy-7,8-dimethyl-2-oxo-2H-chromene-3-yl)-6,7-dimethyl-2-methoxy-2,3-dihydro-4H-furo[3,2-c]chromene-4-one in a 81% yield:

¹H-NMR (300 MHz, DMSO-d₆) δ/ppm: 2.26 (s, 3H); 2.29 (s, 3H); 2.36 (s, 3H); 2.39 (s, 3H); 3.60 (s, 3H); 4.85 (d, J=3.5 Hz, 1H); 6.05 (d, J=3.5 Hz, 1H); 7.17 (d, J=8.2 Hz, 1H); 7.23 (d, J=8.0 Hz, 1H); 7.51 (d, J=8.0 Hz, 1H); 7.74 (d, J=8.2 Hz, 1H);

¹³C-NMR (75.4 MHz, DMSO-d₆) δ/ppm: 11.0; 11.3; 19.6; 19.8; 42.5; 56.3; 100.0; 101.1; 109.7; 113.6; 114.8; 119.2; 120.2; 123.4; 123.9; 125.0; 125.3; 141.4; 142.0; 150.4; 152.8; 158.2; 161.5; 165.5;

ES⁺ m/z: (acetonitrile:water) [MH]⁺: 435.3;

P-38: 3-(4-Hydroxy-6,7-dimethyl-2-oxo-2H-chromene-3-yl)-7,8-dimethyl-2-methoxy-2,3-dihydro-4H-furo[3,2-c]chromene-4-one in a 75% yield:

¹H-NMR (300 MHz, DMSO-d₆) δ/ppm: 2.29 (s, 3H); 2.31-2.33 (bs, 6H) 2.34 (s, 3H); 3.60 (s, 3H); 4.82 (d, J=3.2 Hz, 1H); 6.06 (d, J=3.4 Hz, 1H); 7.19 (s, 1H); 7.27 (s, 1H); 7.55 (s, 1H); 7.77 (s, 1H); 12.00 (bs, 1H);

¹³C-NMR (75.4 MHz, DMSO-d₆) δ/ppm: 18.6; 18.9; 19.5; 19.8; 42.4; 56.4; 100.0; 101.2; 109.4; 113.3; 114.5; 116.6; 122.2; 123.3; 132.4; 133.0; 142.1; 142.7; 150.5; 153.0; 158.4; 161.6; 162.0; 165.1;

ES⁺ m/z: (acetonitrile:water) [MH]⁺: 435.2;

P-39: 3-(4-Hydroxy-5-isopropyl-8-methyl-2-oxo-2H-chromene-3-yl)-9-isopropyl-6-methyl-2-methoxy-2,3-dihydro-4H-furo[3,2-c]chromene-4-one in a 68% yield:

¹H-NMR (300 MHz, DMSO-d₆) δ/ppm: 1.28 (d, J=6.9 Hz, 6H); 1.32 (d, J=6.9 Hz, 6H); 2.26 (s, 3H); 2.32 (s, 3H); 3.59 (s, 3H); 4.03 (sept, J=6.7 Hz, 1H); 4.39 (sept, J=6.8 Hz, 1H); 4.94 (d, J=3.2 Hz, 1H); 6.07 (d, J=3.2 Hz, 1H); 7.26 (d, J=7.9 Hz, 1H); 7.27 (d, J=7.9 Hz, 1H); 7.44 (d, J=8.2 Hz, 1H); 7.51 (d, J=8.0 Hz, 1H); 12.00 (bs, 1H);

¹³C-NMR (75.4 MHz, DMSO-d₆) δ/ppm: 15.3; 15.5; 23.5; 24.3; 24.4; 29.1; 41.4; 56.2; 100.0; 102.4; 110.1; 113.6; 120.6; 121.4; 122.6; 123.2; 132.6; 133.3; 144.3; 146.1; 151.4; 153.5; 157.9; 160.4; 165.0; 166.3;

ES⁺ m/z: (acetonitrile:water) [MH]⁺: 491.3;

P-40: 8-Fluoro-3-(6-fluoro-4-hydroxy-2-oxo-2H-chromene-3-yl)-2-methoxy-2,3-dihydro-4H-furo[3,2-c]chromene-4-one in a 14% yield:

¹H-NMR (300 MHz, DMSO-d₆) δ/ppm: 3.61 (s, 3H); 4.88 (d, J=2.3 Hz, 1H); 6.13 (d, J=3.5 Hz, 1H); 7.45-7.65 (m, 5H); 7.81 (dd, J=9.2 Hz, J=2.8 Hz, 1H);

¹³C-NMR (75.4 MHz, DMSO-d₆) δ /ppm: 42.6; 56.6; 101.3; 102.9; 108.2 (d, J=25.3 Hz); 109.2 (d, J=25.9 Hz); 114.7; 114.8 (d, J=327.7 Hz); 114.9 (d, J=126.9 Hz); 118.5 (d, J=8.6 Hz); 118.9 (d, J=8.6 Hz); 119.8 (d, J=24.6 Hz); 120.4 (d, J=24.7 Hz); 148.5 (d, J=1.5 Hz); 150.8 (d, J=1.7 Hz); 156.3 (d, J=1.4 Hz); 157.9; 159.5 (d, J=3.2 Hz); 161.2; 161.3 (d, J=2.3 Hz); 164.3;

ES⁺ m/z (acetonitrile:water) [MH]⁺ 415.1;

P-41: 3-(4-Hydroxy-6-chloro-2-oxo-2H-chromene-3-yl)-8-chloro-2-methoxy-2,3-dihydro-4H-furo[3,2-c]chromene-4-one in a 25% yield:

¹H-NMR (300 MHz, DMSO-d₆) δ/ppm: 3.61 (s, 3H); 4.88 (bs, 1H); 6.13 (d, J=3.4 Hz, 1H); 7.46 (d, J=8.8 Hz, 1H); 7.55, (d, J=8.9 Hz, 1H); 7.70 (dd, J=8.9 Hz, J=2.5 Hz, 1H); 7.76 (dd, J=8.9 Hz, J=2.6 Hz, 1H); 7.84 (d, J=2.5 Hz, 1H); 8.05 (d, J=2.5 Hz, 1H);

ES⁻ m/z (acetonitrile:water) [M-H]⁻ 444.8;

P-42: 3-(4-Hydroxy-7-chloro-2-oxo-2H-chromene-3-yl)-7-chloro-2-methoxy-2,3-dihydro-4H-furo[3,2-c]chromene-4-one in a 54% yield:

¹H-NMR (300 MHz, DMSO-d₆) δ/ppm: 3.61 (s, 3H); 4.86 (bs, 1H); 6.12 (d, J=3.4 Hz, 1H); 7.49 (m, 2H); 7.61, (d, J=2.0 Hz, 1H); 7.69 (d, J=1.8 Hz, 1H); 7.83 (d, J=8.5 Hz, 1H); 8.01 (d, J=8.6 Hz, 1H);

$^{13}$C-NMR (75.4 MHz, DMSO-d$_6$) δ/ppm: 42.5; 56.6; 101.0; 102.1; 110.9; 114.7; 115.0; 116.4; 116.9; 124.1; 124.4; 124.8; 125.2; 136.7; 137.2; 152.6; 154.8; 157.7; 160.9; 161.7; 164.5;

ES$^+$ m/z (acetonitrile:water) [MH]$^+$ 446.9; 448.9; 450.9;

P-43: 8-Bromo-3-(6-bromo-4-hydroxy-2-oxo-2H-chromene-3-yl)-8-bromo-2-methoxy-2,3-dihydro-4H-furo[3,2-c]chromene-4-one in a 70% yield:

$^1$H-NMR (300 MHz, DMSO-d$_6$) δ/ppm: 3.64 (s, 3H); 4.90 (bs, 1H); 6.15 (d, J=3.4 Hz, 1H); 7.41 (d, J=8.8 Hz, 1H); 7.49, (d, J=8.9 Hz, 1H); 7.84 (dd, J=8.8 Hz, J=2.3 Hz, 1H); 7.89 (dd, J=8.9 Hz, J=2.4 Hz, 1H); 7.98 (d, J=2.3 Hz, 1H); 8.21 (d, J=2.2 Hz, 1H);

$^{13}$C-NMR (75.4 MHz, DMSO-d$_6$) δ/ppm: 42.5; 56.6; 101.0; 102.1; 110.9; 114.7; 115.0; 116.4; 116.9; 124.1; 124.4; 124.8; 125.2; 136.7; 137.2; 152.6; 154.8; 157.7; 160.9; 161.7; 164.5;

ES$^+$ m/z (acetonitrile:water) [MH]$^+$ 534.9; 536.9; 538.8;

P-44: 3-(4,6-Dihydroxy-2-oxo-2H-chromene-3-yl)-8-hydroxy-2-methoxy-2,3-dihydro-4H-furo[3,2-c]chromene-4-one in a 77% yield:

$^1$H-NMR (300 MHz, DMSO-d$_6$) δppm: 3.58 (s, 3H); 4.83 (d, J=2.8 Hz, 1H); 6.05 (d, J=3.4 Hz, 1H); 7.08 (m, 2H); 7.13 (d, J=2.9 Hz, 1H); 7.22 (d, J=8.9 Hz, s, 1H); 7.31 (d, J=9.0 Hz, 1H); 7.34 (t, J=2.7 Hz, 1H); 9.79 (bs, 1H); 9.94 (bs, 1H);

$^{13}$C-NMR (75.4 MHz, DMSO-d$_6$) δ/ppm: 42.6; 56.6; 101.4; 102.9; 113.6; 114.7; 115.9; 116.1; 117.8; 118.7; 119.0; 124.7; 125.9; 135.0; 135.4; 151.2; 153.4; 157.6; 161.0; 163.8;

ES$^+$ m/z (acetonitrile:water) [MH]$^+$ 410.8;

P-45: 3-(4-Hydroxy-6-methoxy-2-oxo-2H-chromene-3-yl)-2,8-dimethoxy-2,3-dihydro-4H-furo[3,2-c]chromene-4-one in a 79% yield:

$^1$H-NMR (300 MHz, DMSO-d$_6$) δ/ppm: 3.63 (s, 3H); 3.83 (s, 3H); 3.89 (s, 3H); 4.86 (bs, 1H); 6.12 (d, J=3.5 Hz, 1H); 7.23 (m, 1H); 7.28 (m, 1H); 7.33 (d, J=3.0 Hz, 1H); 7.37 (d, J=9.0 Hz, 1H); 7.44 (d, J=9.1 Hz, 1H); 7.55 (d, J=2.8 Hz, 1H);

$^{13}$C-NMR (75.4 MHz, DMSO-d$_6$) δ/ppm: 42.6; 55.7; 55.8; 56.6; 101.0; 102.4; 104.1; 105.8; 112.2; 114.6; 117.2; 117.6; 118.0; 120.0; 120.9; 146.9; 148.9; 155.3; 155.5; 158.3; 161.5; 161.8; 164.8;

ES$^-$ m/z: (acetonitrile:water) [M-H]$^-$: 439.3;

P-46: 3-(4-Hydroxy-8-methoxy-2-oxo-2H-chromene-3-yl)-2,6-dimethoxy-2,3-dihydro-4H-furo[3,2-c]chromene-4-one in a 85% yield:

$^1$H-NMR (300 MHz, DMSO-d$_6$) δ/ppm: 3.61 (s, 3H); 3.89 (s, 3H); 3.91 (s, 3H); 4.87 (d, J=2.9 Hz, 1H); 6.10 (d, J=3.5 Hz, 1H); 7.35 (m, 5H); 7.58 (m, 1H);

$^{13}$C-NMR (75.4 MHz, DMSO-d$_6$) δ/ppm: 42.6; 56.1; 56.2; 56.6; 100.9; 102.2; 112.6; 113.7; 114.5; 114.6; 114.7; 114.9; 116.6; 123.9; 124.5; 141.9; 144.0; 146.7; 146.9; 157.9; 161.1; 162.3; 165.3;

ES$^-$ m/z: (acetonitrile:water) [M-H]$^-$: 439.1;

P-47: 3-(4,7-Dihydroxy-5-methyl-2-oxo-2H-chromene-3-yl)-7-hydroxy-9-methyl-2-methoxy-2,3-dihydro-4H-furo[3,2-c]chromene-4-one in a 72% yield:

$^1$H-NMR (300 MHz, DMSO-d$_6$) δ/ppm: 2.61 (s, 3H); 2.66 (s, 3H); 3.17 (s, 3H); 4.79 (d, J=3.4 Hz, 1H); 5.95 (d, J=3.3 Hz, 1H); 6.50 (d, J=2.4 Hz, 1H); 6.59 (d, J=2.1, 2H); 6.63 (d, J=2.8 Hz, 1H); 10.4 (s, 1H); 10.5 (s, 1H); 11.0 (bs, 1H);

$^{13}$C-NMR (75.4 MHz, DMSO-d$_6$,) δ/ppm: 20.8; 23.6; 42.5; 56.3; 96.9; 98.5; 100.0; 100.4; 103.5; 107.1; 113.9; 115.1; 115.3; 116.1; 137.2; 139.0; 155.4; 157.5; 158.4; 160.0; 162.4; 165.0; 166.7;

ES$^-$ m/z (acetonitrile:water) [M-H]$^-$ 438.9;

P-48: 3-(4,7-Dihydroxy-8-methyl-2-oxo-2H-chromene-3-yl)-7-hydroxy-6-methyl-2-methoxy-2,3-dihydro-4H-furo[3,2-c]chromene-4-one in a 12% yield:

$^1$H-NMR (300 MHz, DMSO-d$_6$) δ/ppm: 2.12 (s, 3H); 2.15 (s, 3H); 3.57 (s, 3H); 4.76 (bs, 1H); 6.0 (bs, 1H); 6.86 (d, J=8.8 Hz, 1H); 6.92 (d, J=8.6 Hz, 1H); 7.48 (d, J=8.5 Hz, 1H); 7.69 (d, J=8.8 Hz, 1H); 10.45 (s, 1H); 10.57 (s, 1H); 11.70 (bs, 1H);

$^{13}$C-NMR (75.4 MHz, DMSO-d$_6$) δ/ppm: 7.9; 8.2; 42.1; 56.4; 97.5; 98.3; 103.9; 107.8; 110.3; 111.1; 111.4; 111.9; 114.6; 120.5; 121.4; 151.9; 154.4; 158.7; 159.0; 161.9; 162.7; 165.8;

ES$^-$ m/z (acetonitrile:water) [M-H]$^-$ 436.9;

P-49: 3-(4-Hydroxy-2-oxo-2H-benzo[g]-chromene-3-yl)-2-methoxy-2,3-dihydro-4H-benzo[g]furo[3,2-c]chromene-4-one in a 80% yield:

$^1$H-NMR (300 MHz, DMSO-d$_6$) δ/ppm: 3.69 (s, 3H); 5.02 (d, J=2.0 Hz, 1H); 6.24 (d, J=3.5 Hz, 1H); 7.54-7.71 (m, 4H); 7.90 (s, 1H); 7.98 (s, 1H); 7.99-8.10 (m, 3H); 8.21 (d, J=7.9 Hz, 1H); 8.51 (s, 1H); 8.67 (s, 1H);

$^{13}$C-NMR (75.4 MHz, DMSO-d$_6$,) δppm: 43.0; 56.7; 101.2; 102.9; 111.8; 112.1; 112.4; 114.7; 116.2; 123.1; 124.3; 125.7; 125.9; 127.1; 127.4; 128.4; 128.6; 128.7; 129.1; 129.2; 134.4; 134.6; 148.5; 150.3; 158.4; 161.5; 161.6; 164.6;

Method C

P-50: Sodium salt of 2-ethoxy-3-(4-hydroxy-2-oxo-2H-chromene-3-yl)-2,3-dihydro-4H-furo[3,2-c]chromene-4-one 2-Ethoxy-3-(4-hydroxy-2-oxo-2H-chromene-3-yl)-2,3-dihydro-4H-furo-[3,2-c]chromene-4-one (98 mg; 0.25 mmole) was dissolved in water (8 mL) and 1M sodium hydroxide solution (250 μL; 0.25 mmole) was added. The solution was filtered through Millipore filter and then lyophilized, whereat 94 mg (91%) of a white powdery product were obtained:

$^1$H-NMR (300 MHz, DMSO-d$_6$) δ/ppm: 1.21 (t, J=7.0 Hz, 3H); 3.73 (m, 1H); 3.94 (m, 1H); 4.34 (d, J=2.1 Hz, 1H); 5.93 (d, J=3.6 Hz, 1H); 7.05-7.12 (m, 2H); 7.61-7.67 (m, 1H); 7.73-7.79 (m, 2H).

What is claimed is:

1. A compound of the formula (I)

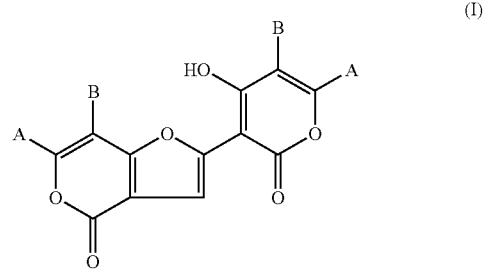

(I)

wherein

A and B taken together with the carbon atoms to which the are attached, each independently represent an aromatic moiety, which is unsubstituted or substituted by one or more substituents which are each independently selected from the group consisting of halogen, $C_1$-$C_4$-alkyl, $C_2$-$C_4$-alkenyl, $C_2$-$C_4$-alkynyl, halo-$C_1$-$C_4$-alkyl, hydroxy, $C_1$-$C_4$-alkoxy, trifluoromethoxy, $C_1$-$C_4$-alkanoyl, amino, amino-$C_1$-$C_4$-alkyl, N-($C_1$-$C_4$-alkyl)amino, N,N-di($C_1$-$C_4$-alkyl)amino, sulfanyl, $C_1$-$C_4$-alkylsulfanyl, sulfo, $C_1$-$C_4$-alkylsulfo, sulfino, $C_1$-$C_4$-alkylsulfino, carboxy, $C_1$-$C_4$-alkoxycarbonyl, cyano, and nitro, or a tautomer, or pharamaceutically acceptable salt thereof.

2. The compound according to claim 1, wherein the aromatic moiety represented by A and B taken together with the carbon atoms to which they are attached are the same.

3. The compound according to claim 2, wherein the aromatic moiety is benzene or naphthalene.

4. The compound according to claim 2, wherein each aromatic moiety is substituted with one or two substituents independently selected from $C_1$-$C_4$ alkyl, hydroxy, methoxy and halogen.

5. The compound according to claim 4, wherein each aromatic moiety is substituted with the same one or two substituents present in an identical position on each moiety.

6. The compound according to claim 4, wherein the $C_1$-$C_4$ alkyl group is independently selected from methyl, ethyl or isopropyl.

7. The compound according to claim 1, wherein A and B taken together with the carbon atoms to which they are attached is an aromatic moiety selected from the group consisting of:
  (a) benzene that is unsubstituted or substitued by one or two substituents independently selected from the group consisting of methyl, ethyl, isopropyl, hydroxy, methoxy, and halogen; and
  (b) unsubstituted naphthalene,
wherein the aromatic moieties represented by A and B taken together with the carbon atoms to which they are attached are identical.

8. The compound according to claim 1, which is selected from the group consisting of:
  2-(4-Hydroxy-2-oxo-2H-chromene-3-yl)-4H-furo[3,2-c]chromene-4-one;
  2-(4-Hydroxy-6-methyl-2-oxo-2H-chromene-3-yl)-8-methyl-4H-furo-[3,2-c]chromene-4-one;
  2-(4-Hydroxy-7-methyl-2-oxo-2H-chromene-3-yl)-7-methyl-4H-furo-[3,2-c]chromene-4-one;
  2-(4-Hydroxy-8-methyl-2-oxo-2H-chromene-3-yl)-6-methyl-4H-furo-[3,2-c]chromene-4-one;
  8-Ethyl-2-(6-ethyl-4-hydroxy-2-oxo-2H-chromene-3-yl)-4H-furo-[3,2-c]chromene-4-one;
  6-Ethyl-2-(8-ethyl-4-hydroxy-2-oxo-2H-chromene-3-yl)-4H-furo-[3,2-c]chromene-4-one;
  2-(4-Hydroxy-6-isopropyl-2-oxo-2H-chromene-3-yl)-8-isopropyl-4H-furo-[3,2-c]chromene-4-one;
  2-(4-Hydroxy-8-isopropyl-2-oxo-2H-chromene-3-yl)-6-isopropyl-4H-furo-[3,2-c]chromene-4-one;
  2-(4-Hydroxy-5,7-dimethyl-2-oxo-2H-chromene-3-yl)-7,9-dimethyl-4H-furo-[3,2-c]chromene-4-one;
  2-(4-Hydroxy-6,7-dimethyl-2-oxo-2H-chromene-3-yl)-7,8-dimethyl-4H-furo-[3,2-c]chromene-4-one;
  2-(4-Hydroxy-5,8-dimethyl-2-oxo-2H-chromene-3-yl)-6,9-dimethyl-4H-furo-[3,2-c]chromene-4-one;
  2-(4,5-Dihydroxy-2-oxo-2H-chromene-3-yl)-9-hydroxy-4H-furo-[3,2-c]chromene-4-one;
  2-(4,7-Dihydroxy-5-methyl-2-oxo-2H-chromene-3-yl)-7-hydroxy-9-methyl-4H-furo[3,2-c]chromene-4-one;
  7,9-Dihydroxy-2-(4,5,7-trihydroxy-2-oxo-2H-chromene-3-yl)-4H-furo-[3,2-c]chromene-4-one;
  2-(4-Hydroxy-6-methoxy-2-oxo-2H-chromene-3-yl)-8-methoxy-4H-furo-[3,2-c]chromene-4-one;
  2-(4-Hydroxy-7-methoxy-2-oxo-2H-chromene-3-yl)-7-methoxy-4H-furo-[3,2-c]chromene-4-one;
  8-Fluoro-2-(6-fluoro-4-hydroxy-2-oxo-2H-chromene-3-yl)-4H-furo-[3,2-c]chromene-4-one;
  2-(4-Hydroxy-6-chloro-2-oxo-2H-chromene-3-yl)-8-chloro-4H-furo-[3,2-c]chromene-4-one;
  8-Bromo-2-(6-bromo-4-hydroxy-2-oxo-2H-chromene-3-yl)-4H-furo-[3,2-c]chromene-4-one;
  2-(4-Hydroxy-7-chloro-2-oxo-2H-chromene-3-yl)-7-chloro-4H-furo-[3,2-c]chromene-4-one;
  2-(4-Hydroxy-6-chloro-7-methyl-2-oxo-2H-chromene-3-yl)-8-chloro-7-methyl-4H-furo[3,2-c]chromene-4-one;
  2-(4-Hydroxy-8-chloro-5-methyl-2-oxo-2H-chromene-3-yl)-6-chloro-9-methyl-4H-furo[3,2-c]chromene-4-one;
  2-(1-Hydroxy-3-oxo-3H-benzo[f]chromene-2-yl)-4H-benzo[f]furo-[3,2-c]chromene-4-one
  Sodium salt of 2-(4-hydroxy-2-oxo-2H-chromene-3-yl)-4H-furo[3,2-c]chromene-4-one;
  7-Ethyl-2-(7-ethyl-4-hydroxy-2-oxo-2H-chromene-3-yl)-4H-furo-[3,2-c]chromene-4-one
  2-(4,6-Dihydroxy-2-oxo-2H-chromene-3-yl)-8-hydroxy-4H-furo-[3,2-c]chromene-4-one;
  2-(4,7-Dihydroxy-2-oxo-2H-chromene-3-yl)-7-hydroxy-4H-furo-[3,2-c]chromene-4-one;
  2-(4-Hydroxy-8-methoxy-2-oxo-2H-chromene-3-yl)-6-methoxy-4H-furo-[3,2-c]chromene-4-one;
  2-(4-Hydroxy-2-oxo-2H-benzo[g]chromene-3-yl)-4H-benzo[g]furo-[3,2-c]chromene-4-one;
  2-(4-Hydroxy-6,8-dichloro-2-oxo-2H-chromene-3-yl)-6,8-dichloro-4H-furo-[3,2-c]chromene-4-one;
  2-(4-Hydroxy-7,8-dimethyl-2-oxo-2H-chromene-3-yl)-6,7-dimethyl-4H-furo-[3,2-c]chromene-4-one
  2-(4-Hydroxy-6,8-dimethyl-2-oxo-2H-chromene-3-yl)-6,8-dimethyl-4H-furo-[3,2-c]chromene-4-one,
  and tautomers, pharmaceutically acceptable salts thereof.

9. A pharmaceutical composition comprising a compound according to claim 1 and a pharmaceutically acceptable diluent or carrier.

10. A process for the preparation of a compound according to claim 1, comprising reacting a compound of the formula (II)

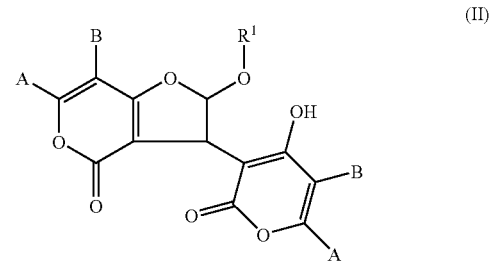

wherein $R^1$ is hydrogen, methyl or ethyl, and A and B are the same as defined in claim 1, in an acidic medium at a reaction temperature of from about room temperature to about 150° C.

11. The process according to claim 10, wherein the acidic medium comprises acetic acid.

12. The process according to claim 11, wherein the reaction temperature is the boiling temperature of acetic acid.

13. A method of treating an allergic disease or condition selected from allergic asthma, allergic rhinitis, allergic eczema, allergic dermatitis, allergic neurodermatitis, and allergic conjunctivitis.

14. The method of claim 13, wherein the disease or condition is allergic asthma.

* * * * *